US011865266B2

(12) United States Patent
Holley et al.

(10) Patent No.: US 11,865,266 B2
(45) Date of Patent: Jan. 9, 2024

(54) GAS FLOW REGULATING APPARATUS FOR RESPIRATORY TREATMENT

(71) Applicant: ResMed Pty Ltd, Bella Vista (AU)

(72) Inventors: Liam Holley, Sydney (AU); Barton John Kenyon, Sydney (AU); Gordon Joseph Malouf, Sydney (AU); Luke Andrew Stanislas, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 320 days.

(21) Appl. No.: 17/206,732

(22) Filed: Mar. 19, 2021

(65) Prior Publication Data

US 2021/0213236 A1    Jul. 15, 2021

Related U.S. Application Data

(63) Continuation of application No. 15/740,088, filed as application No. PCT/AU2016/050564 on Jun. 30, 2016, now Pat. No. 11,007,343.
(Continued)

(30) Foreign Application Priority Data

Jun. 30, 2015  (AU) .............................. 2015902539

(51) Int. Cl.
*A61M 16/20*  (2006.01)
*A61M 16/06*  (2006.01)
*A61M 16/00*  (2006.01)

(52) U.S. Cl.
CPC ........ *A61M 16/20* (2013.01); *A61M 16/0066* (2013.01); *A61M 16/0093* (2014.02);
(Continued)

(58) Field of Classification Search
CPC .... A61M 16/06; A61M 16/20; A61M 16/208; A61M 16/206; A61M 16/08;
(Continued)

(56) References Cited

U.S. PATENT DOCUMENTS 4,642,833 A   2/1987   Stoltz
5,791,339 A   8/1998   Winter
(Continued)

FOREIGN PATENT DOCUMENTS

WO   WO 98/004310 A1   2/1998
WO   WO 98/034665 A1   8/1998
(Continued)

OTHER PUBLICATIONS

"Respiratory Physiology", by John B. West, Lippincott Williams & Wilkins, 9$^{th}$ edition published 2012 (8 pages).
(Continued)

*Primary Examiner* — Margaret M Luarca
(74) *Attorney, Agent, or Firm* — Nixon & Vanderhye P.C.

(57) ABSTRACT

A flow regulating valve for a respiratory treatment system is disclosed, as well as a vent arrangement comprising the flow regulating valve. The flow regulating valve may include an inlet, an outlet, and a variable conduit in fluid communication with the inlet and the outlet. The variable conduit may include a movable portion that may move to vary an impedance of the variable conduit, thereby regulating a flow rate of the air travelling through the variable conduit. Advantageously, the flow regulating valve may thus reduce wastage of air (e.g. humidified air) that is exhausted from a respiratory treatment system, while maintaining sufficient washout of air.

24 Claims, 31 Drawing Sheets

Related U.S. Application Data

(60) Provisional application No. 62/356,096, filed on Jun. 29, 2016.

(52) U.S. Cl.
CPC ........ *A61M 16/06* (2013.01); *A61M 16/0683* (2013.01); *A61M 16/0003* (2014.02); *A61M 16/208* (2013.01)

(58) Field of Classification Search
CPC .... A61M 16/0866; A62B 18/02; A62B 18/10; A62B 9/02; F16K 7/07; F16K 7/075
See application file for complete search history.

(56) References Cited

U.S. PATENT DOCUMENTS

| | | | |
|---|---|---|---|
| 5,937,855 | A | 8/1999 | Zdrojkowski |
| 2014/0020687 | A1 | 1/2014 | Cullen et al. |
| 2014/0246025 | A1 | 9/2014 | Cragg |
| 2014/0283831 | A1 | 9/2014 | Foote |
| 2014/0305431 | A1 | 10/2014 | Holley et al. |
| 2018/0185607 | A1 | 7/2018 | Holley et al. |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 | 2/2013 |
| WO | WO 2014/186584 | 11/2014 |

OTHER PUBLICATIONS

International Search Report for PCT/AU2016/050564 dated Oct. 11, 2016, 4 pages.
Written Opinion of the ISA for PCT/AU2016/050564 dated Oct. 11, 2016, 6 pages.
International Preliminary Report on Patentability for PCT/AU2016/050564 dated Oct. 20, 2017, 17 pages.

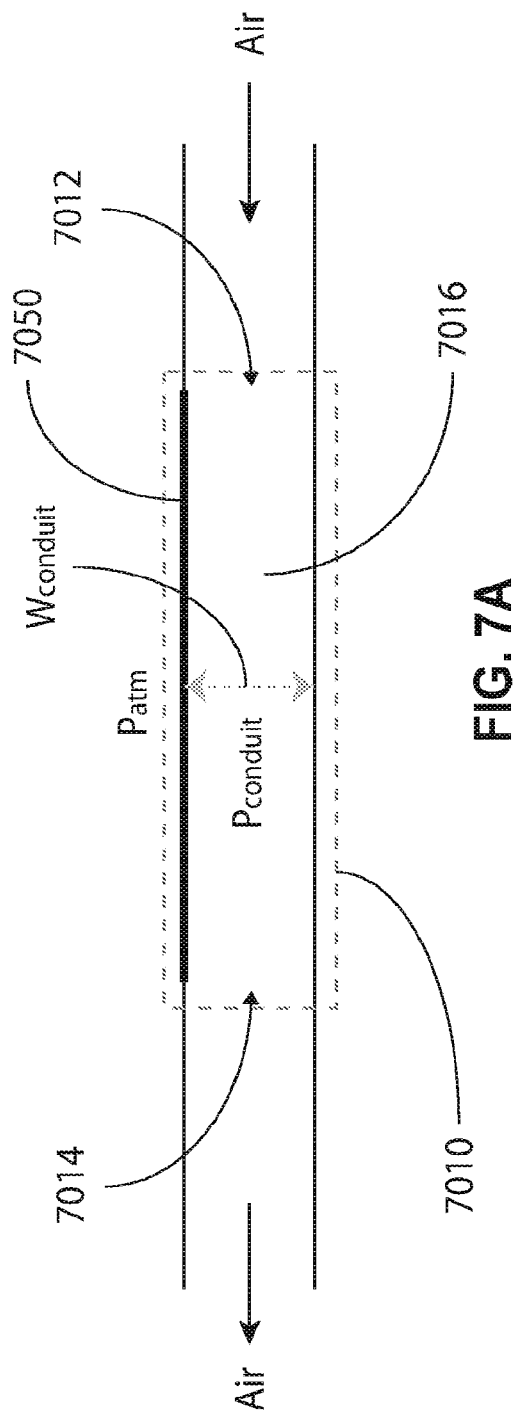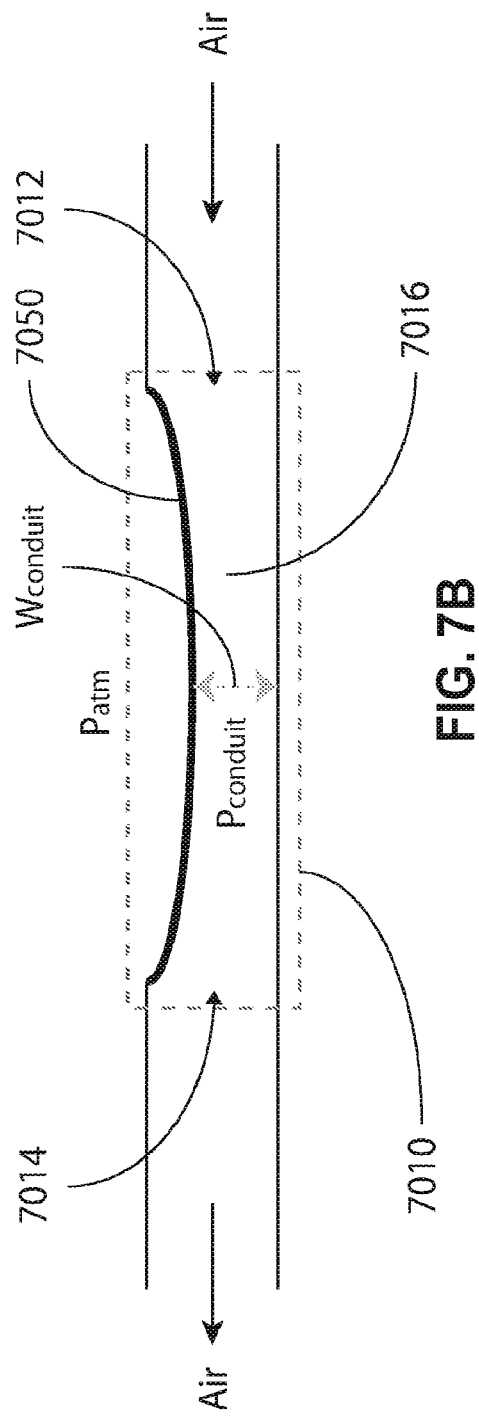

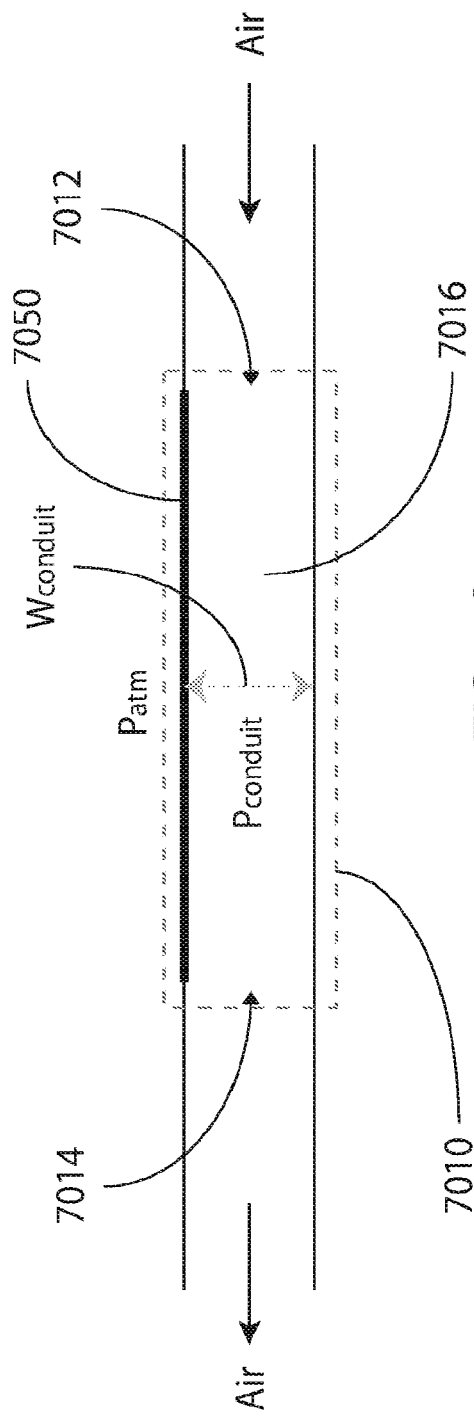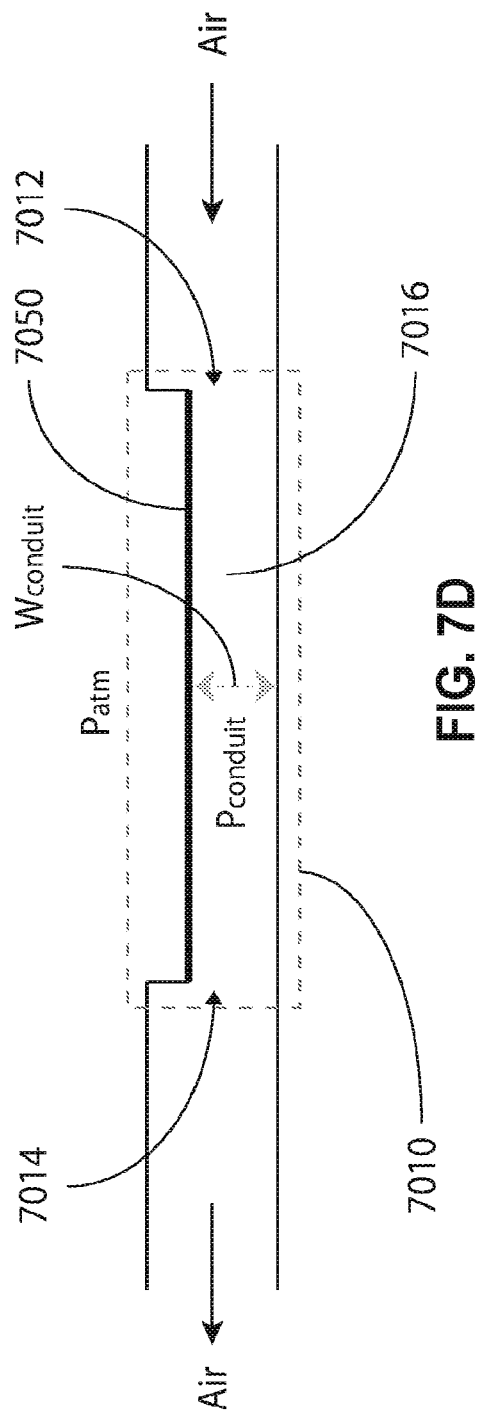

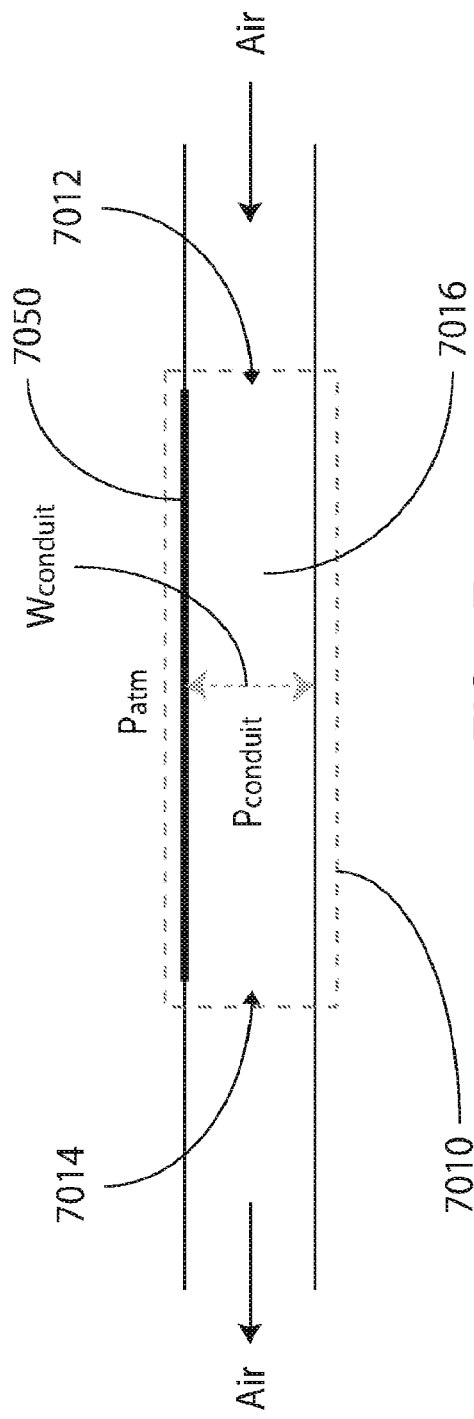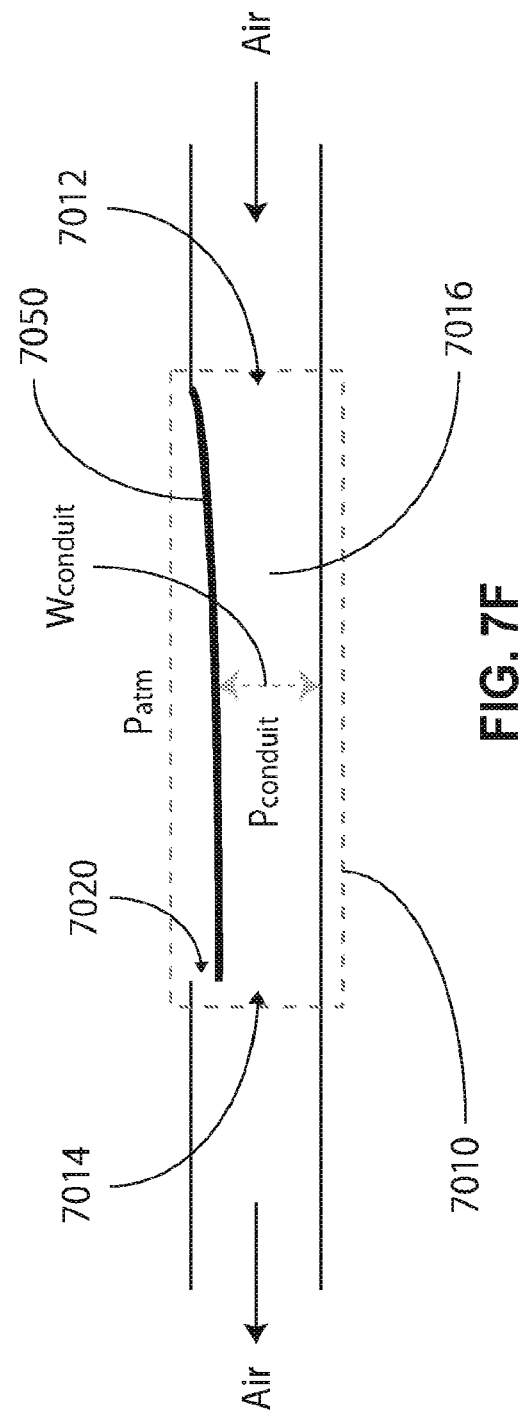

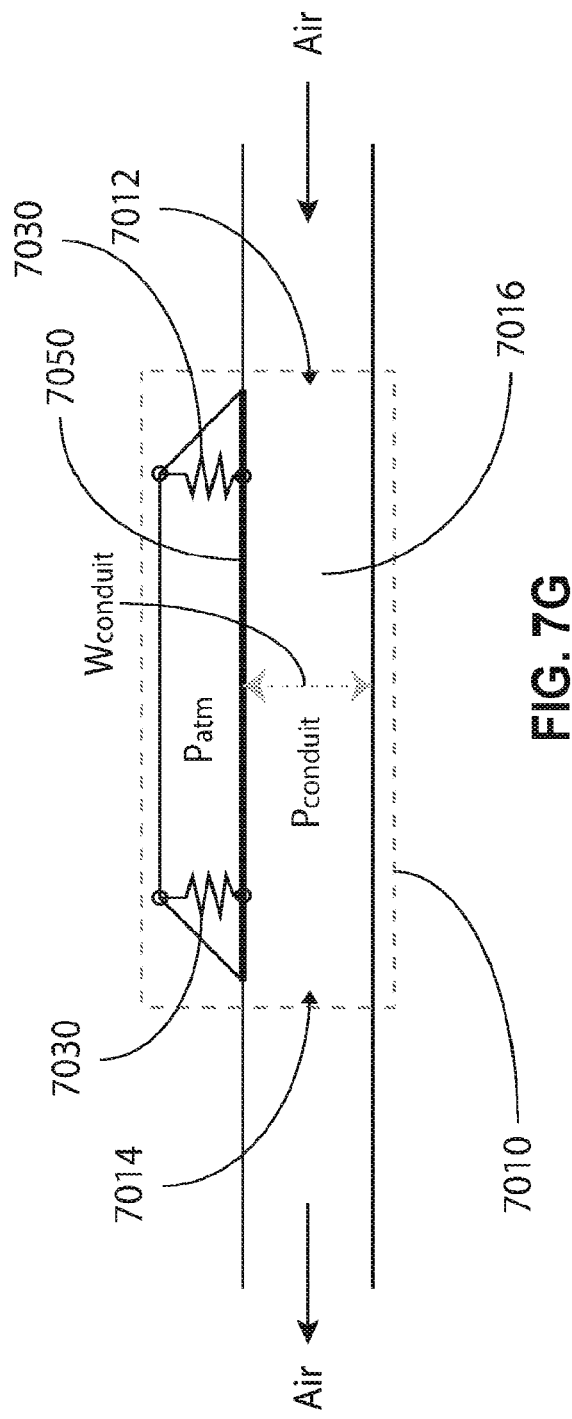
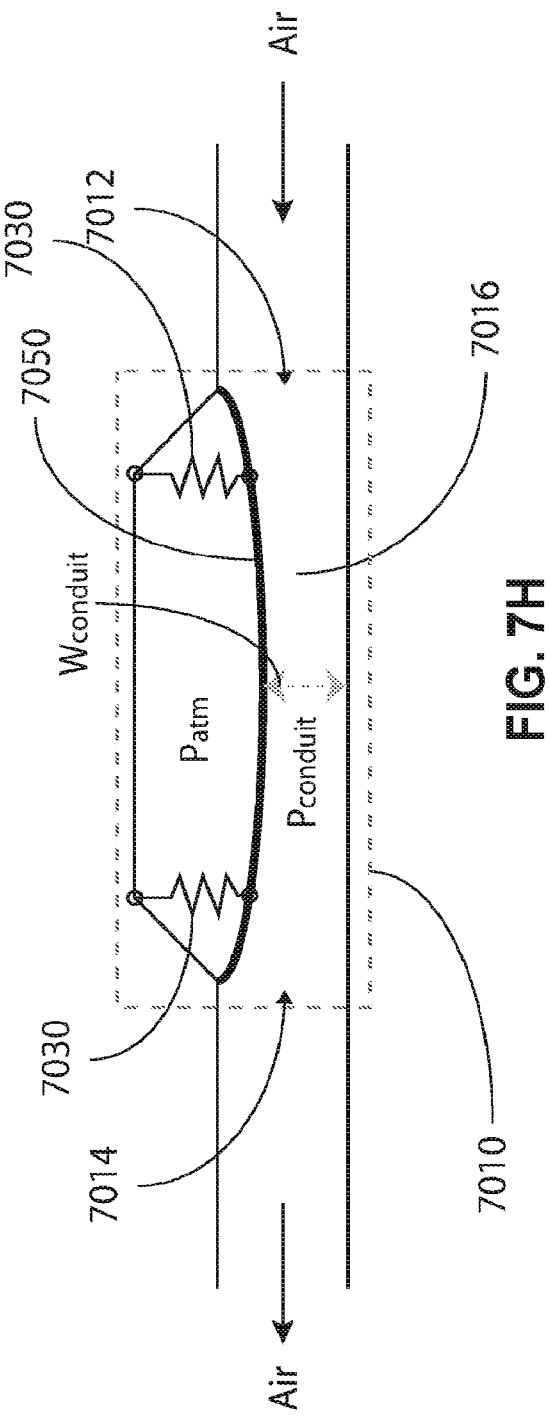
FIG. 7G
FIG. 7H

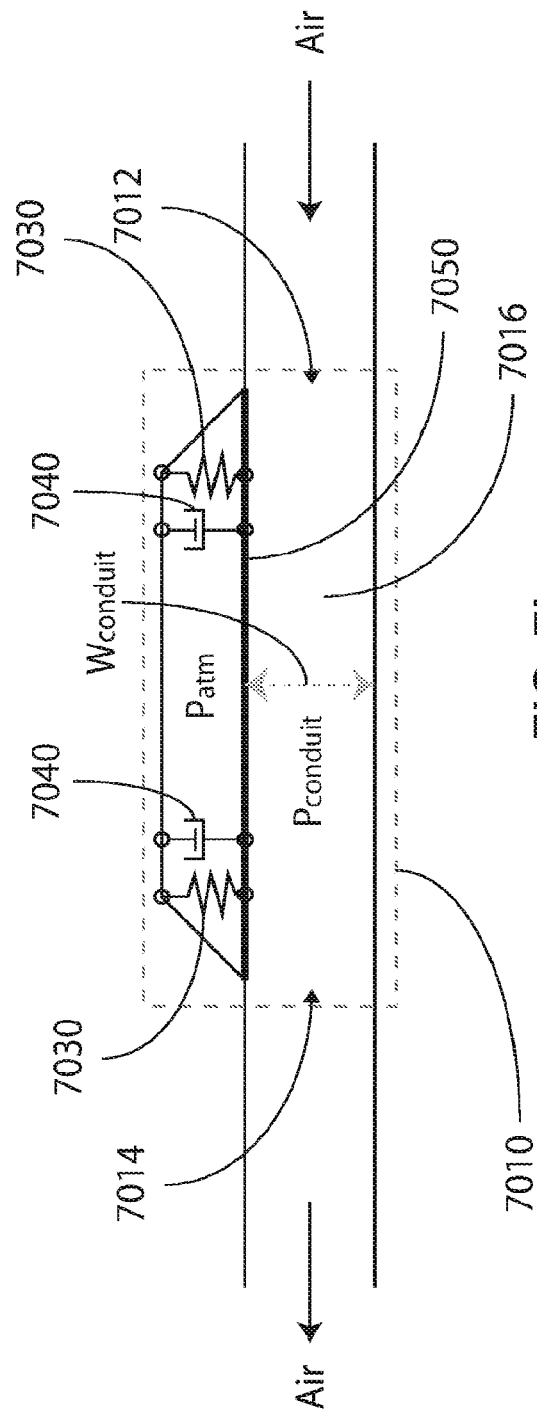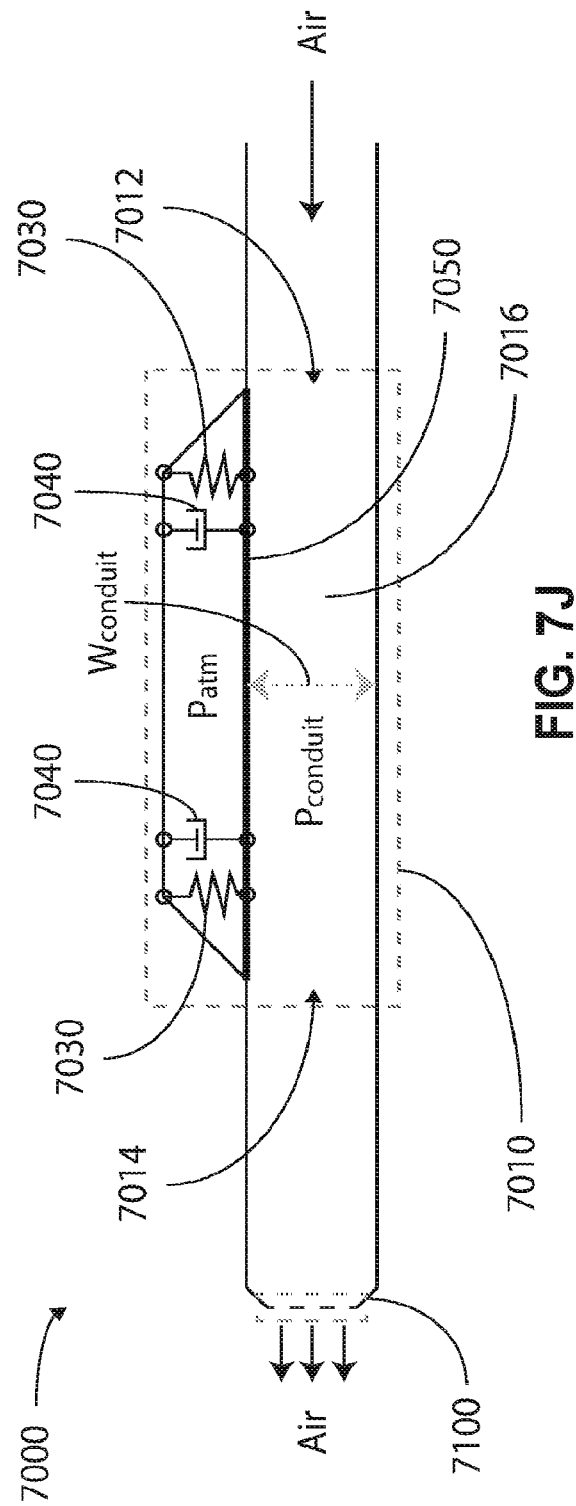

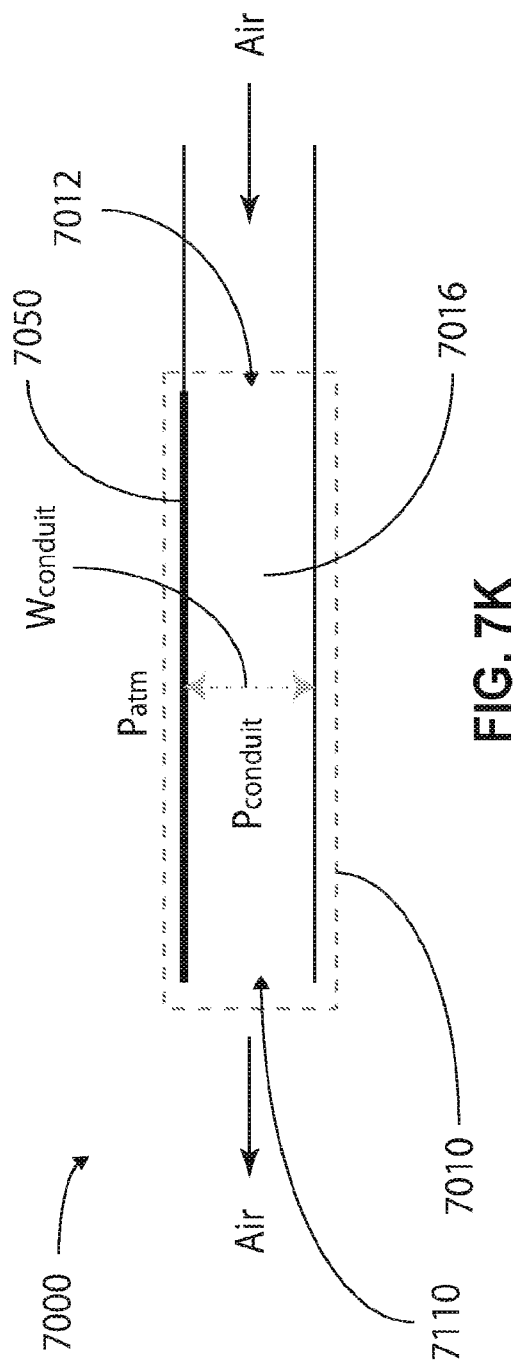
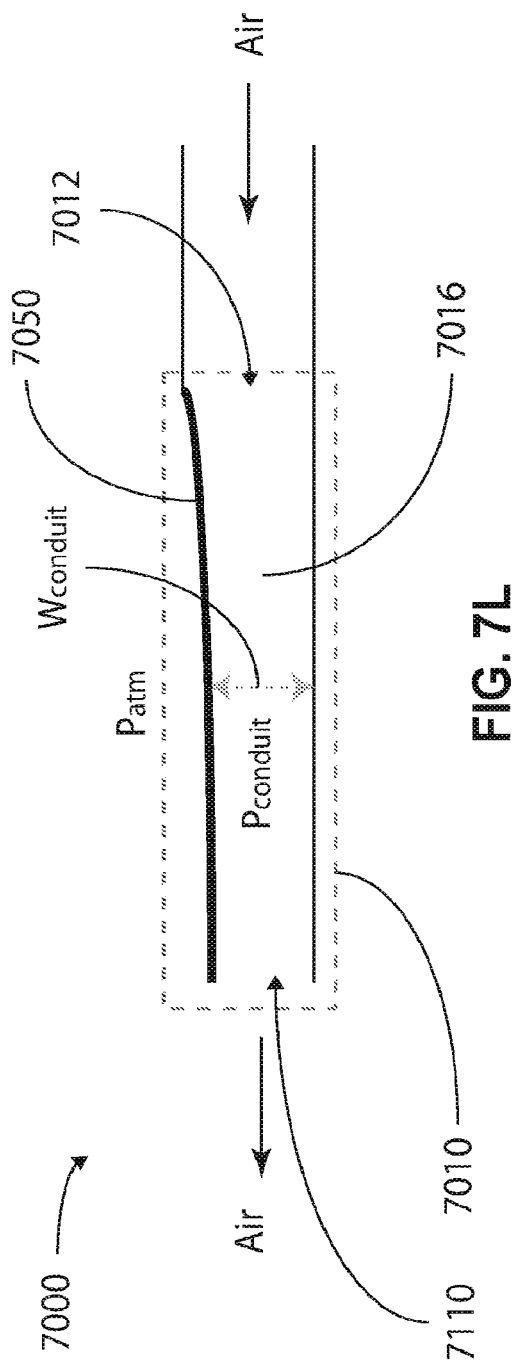
FIG. 7K
FIG. 7L

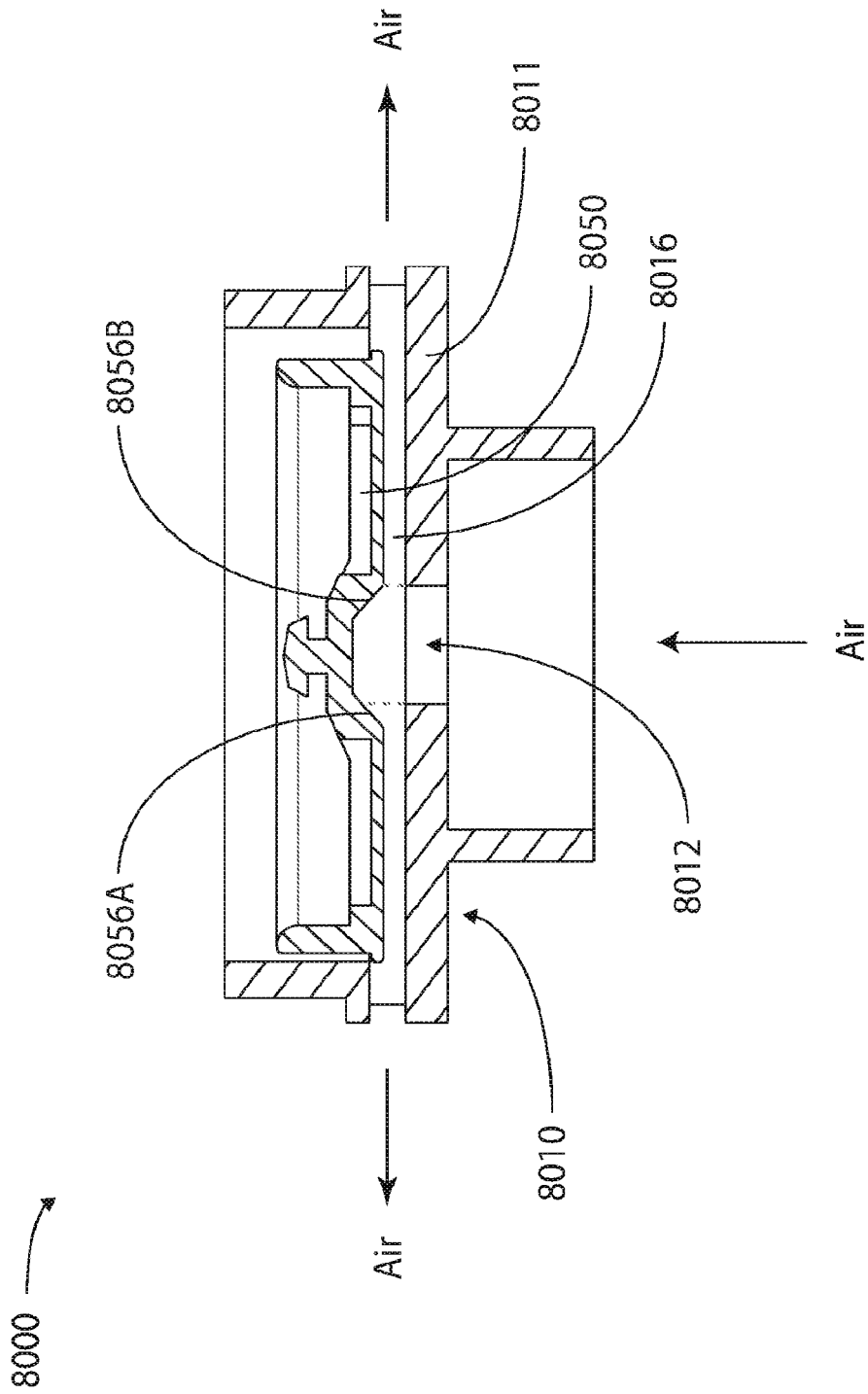

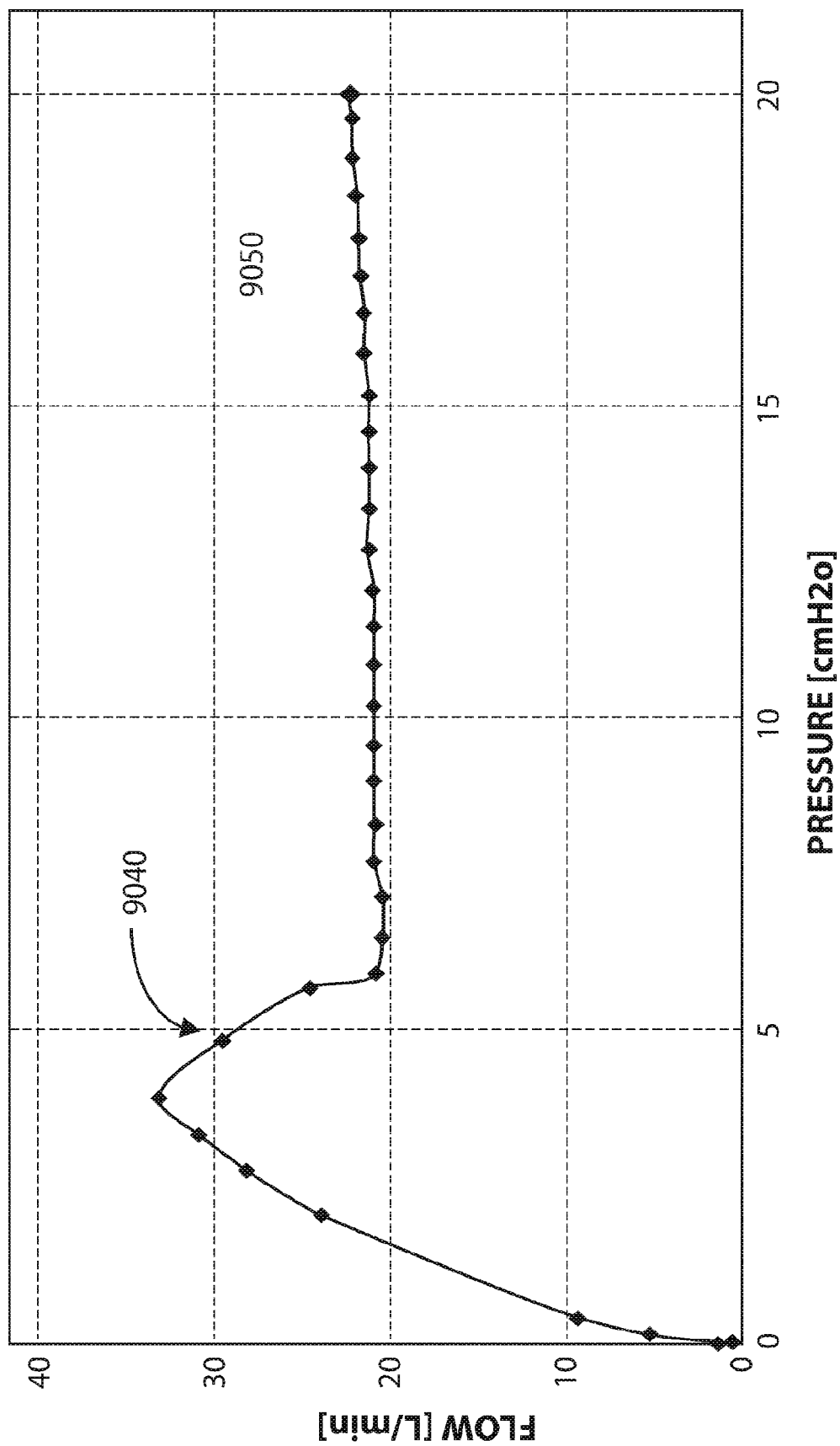

GAS FLOW REGULATING APPARATUS FOR RESPIRATORY TREATMENT

This application is a continuation of U.S. application Ser. No. 15/740,088, filed Dec. 27, 2017, now allowed, which is the U.S. national phase of International Application No. PCT/AU2016/050564 filed Jun. 30, 2016 which designated the U.S. and claims priority to AU Patent Application No. 2015902539 and the benefit of U.S. Provisional Application No. 62/356,096 filed Jun. 29, 2016, the entire contents of each of which are hereby incorporated by reference in its entirety.

A portion of the disclosure of this patent document contains meterial which is subject to copyright protection. The copyright owner has no objection to the facsimile reproduction by anyone of the patent document or the patent disclosure, as it appears in Patent Office patent files or records, but otherwise reserves all copyright rights whatsoever.

1 BACKGROUND OF THE TECHNOLOGY

1.1 Field of the Technology

The present technology relates to medical devices or apparatus, and their use. More specifically, the present technology relates to a valve or a vent for use in a medical device or apparatus, such as a valve or a vent configured to control and/or regulate a flow of gas, and uses thereof.

1.2 Description of the Related Art

1.2.1 Human Respiratory System and its Disorders

The respiratory system of the body facilitates gas exchange. The nose and mouth form the entrance to the airways of a patient.

A range of respiratory disorders exist. Certain disorders may be characterised by particular events, e.g. apneas, hypopneas, and hyperpneas.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

1.2.3 Treatment Systems

These therapies may be provided by a treatment system or device. Such systems and devices may also be used to diagnose a condition without treating it.

A treatment system may comprise a Respiratory Pressure Therapy device (RPT device), an air circuit, a humidifier, a patient interface, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

1.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

| RPT Device name | A-weighted sound power level (SWL) dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

1.2.3.4 Vent/Valve Technologies

Some forms of treatment systems may include a vent to allow the washout of exhaled carbon dioxide. The vent may allow a flow of gas from an interior space of the patient interface, e.g., the plenum chamber, to an exterior of the patient interface, e.g., to ambient.

A vent may be a part of a patient interface, such as a part of an elbow or a mask wall. In some forms, a vent may form a part of an air circuit. In some forms, a vent may form part of an RPT device. A treatment system may comprise a vent arrangement, for example comprising a plurality of vents at one or more locations.

The vent may comprise an orifice. Gas may flow through the orifice in use, for example during use of the respiratory treatment system and/or during use of a patient interface. Many such vents are noisy. Others may become blocked in use and thus provide insufficient washout. Some vents may be disruptive of the sleep of a bed partner 1100 of the patient 1000, e.g. through noise or focused airflow.

There are a number of requirements for a vent arrangement in a context of a respiratory treatment system. A vent arrangement must allow sufficient washout of exhaled carbon dioxide to allow the patient to breathe in sufficient oxygen. On the other hand, the treatment system must provide a flow of gas at a sufficient flow rate to compensate for any flow of gas exiting the treatment system through the vent arrangement. Thus, it may be beneficial for a vent arrangement to exhaust only the minimum required amounts of gases from respiratory treatment system to allow the patient to breathe in sufficient oxygen.

Furthermore, a vent arrangement in a treatment system may need to operate over a wide range of operating conditions. For example, an RPT device configured to provide CPAP therapy to a patient may be configured to operate over a range of pressures, such as between 4 cm $H_2O$ and 20 cm $H_2O$.

A fixed orifice vent (e.g. disclosed in International Patent Application Publication No. WO 1998/034,665) comprises one or more fixed orifices (e.g. moulded) configured to exhaust a flow of gas. In a fixed orifice vent, the cross-section area of the orifices does not vary throughout its operation. A fixed orifice vent typically behaves such that a flow rate of air travelling therethrough increases as a function of a pressure difference between two sides of the vent.

Thus, a fixed orifice vent is typically configured such that a sufficient gas washout is achieved at the lowest operating pressure (e.g. at 4 cm $H_2O$). As a corollary, when operating at a high pressure (e.g. at 20 cm $H_2O$) the fixed orifice vent exhausts a flow of gas at a flow rate well in excess of the minimum flow rate required for achieving sufficient washout. As a consequence, the RPT device designed for use with a fixed orifice vent is typically configured to provide a sufficiently high flow rate to account for the gases exhausted from the fixed orifice vent. Thus, a capacity of the RPT device, such as a size of the blower or the power supply, may be advantageously reduced if the flow rate through the fixed orifice vent is able to be reduced.

There also exist other types of vent arrangements, such as those comprising a variable orifice, for example comprising adjustable portions that are actuated by a solenoid. An example of such a vent arrangement is described in International Patent Application Publication No. WO 2013/040, 198. In some arrangements, a vent arrangement may be configured to close during an inspiratory portion of a breath cycle and open during an expiratory portion of a breath cycle, such as described in International Patent Application Publication No. WO 2013/067,592.

In some forms, a vent arrangement may be configured to regulate a flow rate of the exhaust gas flow, such as to ameliorate some of the aforementioned challenges. The vent arrangement may for example comprise a flow regulating component or portion (e.g. a valve), which may be configured to substantially regulate a flow rate of gases travelling therethrough across a range of pressures.

Examples of flow regulating components (sometimes referred to as a 'constant flow valve') include those described in U.S. Pat. Nos. 5,685,296, 6,584,977, US Patent Application Publication No. US 2004/0094157, and US Patent Application Publication No. US 2005/0166923.

However, one or more of the prior art flow regulating valves may suffer from one or more shortcomings that may limit their usefulness. One potential such shortcoming may relate to noise. It is well understood that respiratory treatment systems are typically used in proximity to its patient. In some cases, such as PAP therapy, the patient, or the patient's bed partner may be asleep (or attempting to sleep) while using the respiratory treatment system. Thus, noise can be an important consideration to efficacy and commercial success of a respiratory treatment system.

ResMed Limited has developed a number of improved mask vent technologies (e.g. fixed orifice vent technologies). See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. US 2009/0044808.

As shown in the table of noise of prior masks (ISO 17510-2:2007, 10 cm$H_2O$ pressure at 1 m), modern patient interfaces are very quiet (e.g. under 25 dB(A) SPL) even in comparison to a quiet bedroom (e.g. approximately 30 dB(A) SPL). Thus, other components of the respiratory treatment system (such as a flow regulating valve) are preferably sufficiently quiet to not disturb the patient (or the bed partner) in a quiet, bedroom environment.

| Mask name | Mask type | A-weighted sound power level (SWL) dB(A) (uncertainty) | A-weighted sound pressure level (SPL) dB(A) (uncertainty) | Year (approx.) |
| --- | --- | --- | --- | --- |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |

-continued

| | | | | |
|---|---|---|---|---|
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

(* one specimen only, measured using test method specified in ISO 3744 in CPAP mode at 10 cmH$_2$O)Sound pressure values of a variety of objects are listed below.

Another potential shortcoming of the prior art relates to an adjustability of the vent arrangement. For example, the flow regulating valve may be configured to regulate a gas flow rate therethrough, such as at 20 L/min, which may be suitable for a typical patient receiving CPAP therapy. However, the same vent arrangement may not be suitable for a patient who requires a larger gas flow rate, such as if the patient temporarily requires an increased tidal volume.

Still further, a vent arrangement for a respiratory treatment system may be preferably robust against potential occurrence of condensation. Particularly where a humidifier is used in conjunction with an RPT device, condensation may occur from the gas flow. Thus, the vent arrangement may be preferably robust (e.g. not occluded) when condensation occur in or around the vent arrangement, such as in the flow regulating valve.

Furthermore, a designer of the vent arrangement must manage still other requirements such as cost, manufacturability, size, reliability and robustness, some or all of which may conflict with each other.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One aspect of the present technology relates to a valve for regulating a flow of gas in a respiratory apparatus, the valve comprising an inlet to receive gases, an outlet to deliver gases, a valve body, a movable portion comprising a first side and a second side and a variable conduit configured to deliver the flow of gas from the inlet to the outlet, the variable conduit defined at least in part by the valve body and the first side of the movable portion, wherein the second side of the movable portion is isolated from the flow of gas, and the movable portion is configured move to change an impedance of the variable conduit based on air pressures at the first side and the second side.

According to one aspect of the present technology, the movable portion is circular.

According to one aspect of the present technology, the second side of the movable portion is located in ambient air.

According to one aspect of the present technology, the movable portion is biased away from the valve body.

According to one aspect of the present technology, the valve further comprises a spring biasing the movable portion away from the valve body.

According to one aspect of the present technology, the inlet is perpendicular to the variable conduit.

According to one aspect of the present technology, the variable conduit comprises an increasing size from the inlet towards the outlet.

According to one aspect of the present technology, the variable conduit is configured as a cylinder.

According to one aspect of the present technology, the valve further comprises a damper coupled to the movable portion.

According to one aspect of the present technology, the inlet is perpendicular to the first side of the movable portion.

According to one aspect of the present technology, the valve further comprises an entrainment port to entrain atmospheric air using the flow of gas.

According to one aspect of the present technology, the movable portion at least partly comprises the entrainment port.

According to one aspect of the present technology, the valve body and the first side of the movable portion are parallel to each other.

According to one aspect of the present technology, the first side of the movable portion comprises a stabilising recess.

According to one aspect of the present technology, the valve further comprises an additional movable portion positioned adjacent the second side of the first movable portion.

One aspect of the present technology relates to a patient interface for a respiratory apparatus. The patient interface comprises a seal-forming structure with a seal-forming surface. The patient interface further comprises a plenum chamber. In addition, the patient interface comprises a valve as discussed above. The valve is configured to vent gas from the plenum chamber.

One aspect of the present technology relates to a vent arrangement for washout of gases from a respiratory apparatus, the vent arrangement comprising a gas inlet for receiving a flow of gas, a gas outlet for delivering the flow of gas, a valve comprising a flow surface and a reference surface, a valve housing and a conduit configured to deliver the flow of gas from the gas inlet to the gas outlet, the conduit defined at least partly by the flow surface and the valve housing, wherein the reference surface is separated from the flow of gas and the valve is movable to vary a size of the conduit based on pressures on the flow surface and pressures on the reference surface.

According to one aspect of the present technology, the flow surface is circular.

According to one aspect of the present technology, the reference surface is exposed to the atmosphere.

According to one aspect of the present technology, the conduit is cylindrically shaped.

According to one aspect of the present technology, the gas outlet is disposed on a circumference of the cylindrically shaped conduit.

According to one aspect of the present technology, the vent arrangement further comprises a spring coupled to the valve.

According to one aspect of the present technology, the spring is a leaf spring.

According to one aspect of the present technology, the vent arrangement further comprises a damper coupled to the valve.

According to one aspect of the present technology, the vent arrangement further comprises an additional movable valve positioned adjacent the reference side of the first movable valve.

One aspect of the present technology relates to a patient interface for a respiratory apparatus. The patient interface comprises a seal-forming structure with a seal-forming surface. The patient interface further comprises a plenum chamber. In addition, the patient interface comprises the vent arrangement as discussed above. The vent arrangement is configured to vent gas from the plenum chamber.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1 shows a system including a patient 1000 wearing a patient interface 3000, in the form of a nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown.

3.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

3.3 Patient Interface

FIG. 3 shows a patient interface in the form of a nasal mask in accordance with one form of the present technology.

3.4 RPT Device

3.5 Humidifier

Figure 5A:
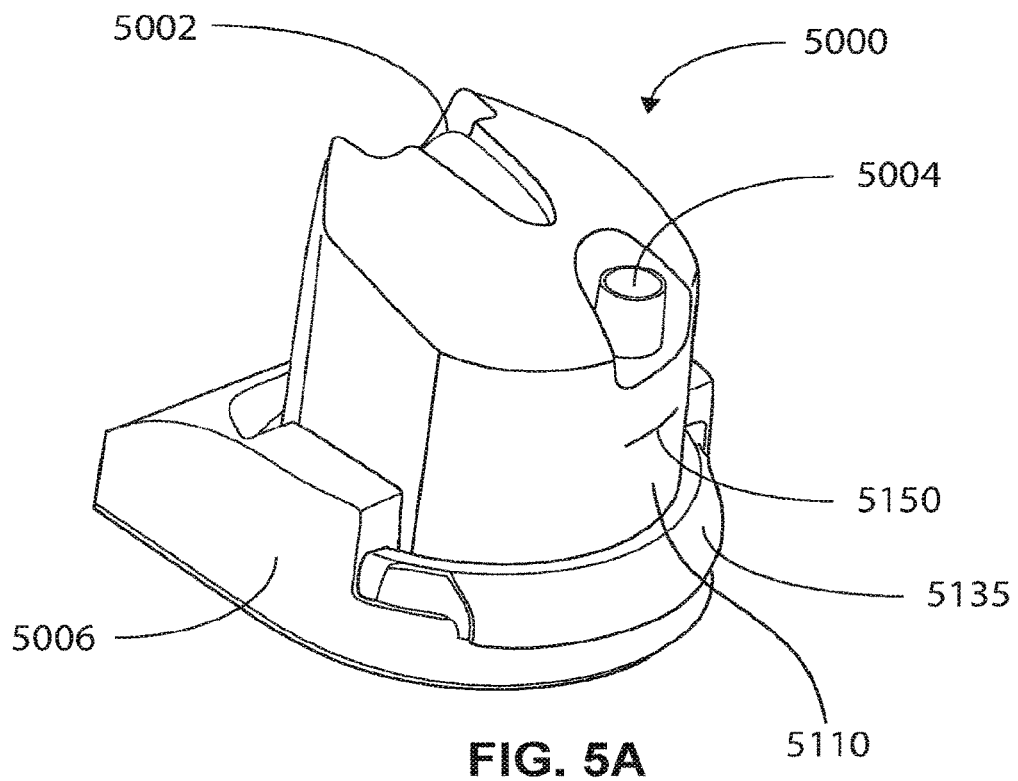

FIG. 5A shows an isometric view of a humidifier in accordance with one form of the present technology.

Figure 5B:
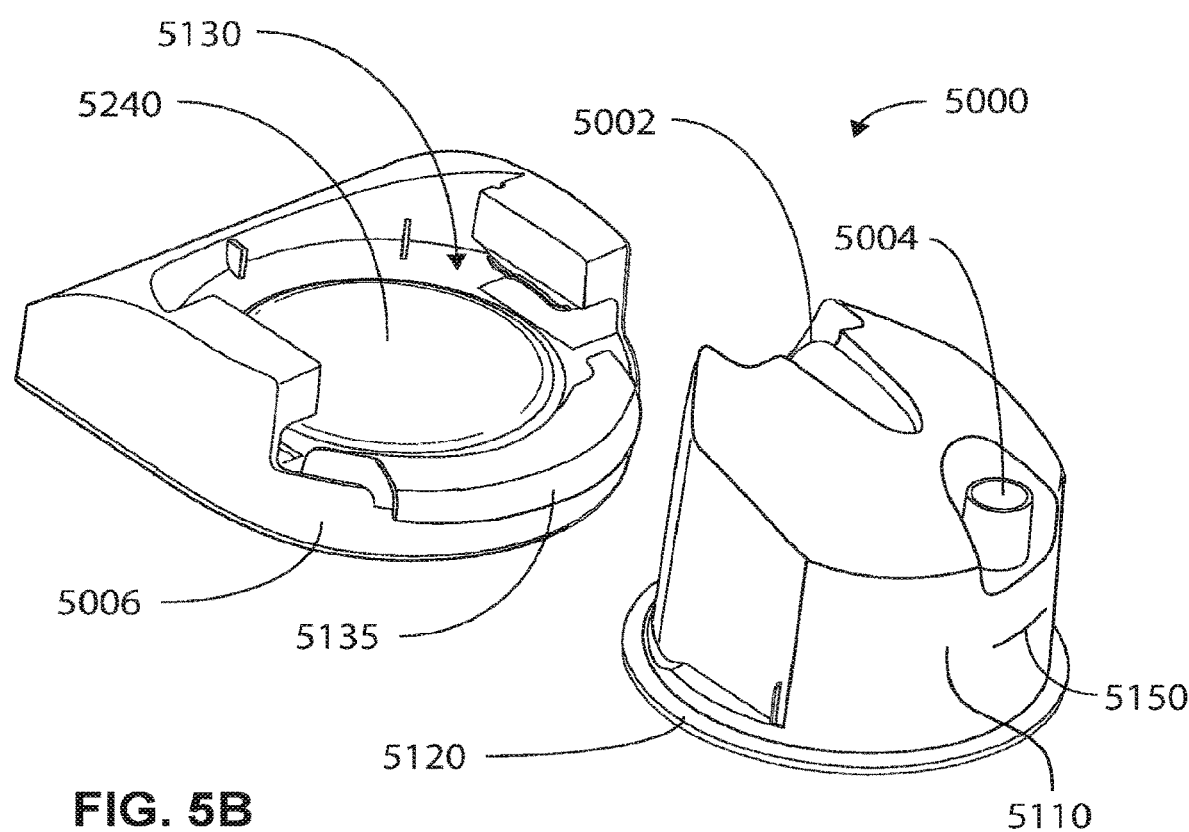

FIG. 5B shows an isometric view of a humidifier in accordance with one form of the present technology, showing a humidifier reservoir 5110 removed from the humidifier reservoir dock 5130.

3.6 Breathing Waveforms

Figure 6:
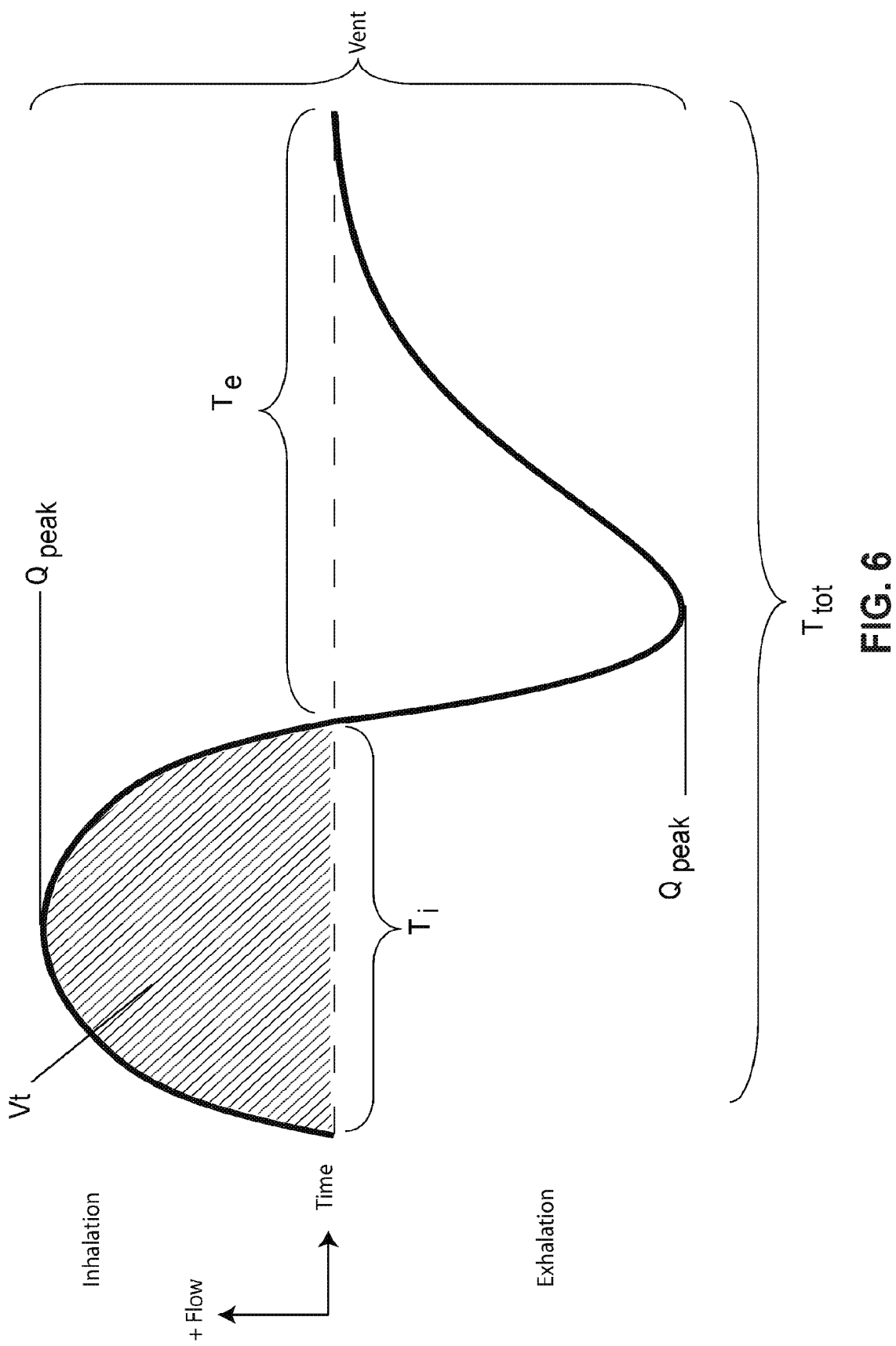

FIG. 6 shows a model typical breath waveform of a person while sleeping.

3.7 Vent/Valve

FIG. 7A shows a schematic view of a flow regulating valve according to one form of the present technology.

FIG. 7B shows a schematic view of a flow regulating valve according to one form of the present technology, showing the movable portion in a deformed configuration.

FIG. 7C shows a schematic view of a flow regulating valve according to one form of the present technology.

FIG. 7D shows a schematic view of a flow regulating valve according to one form of the present technology, showing the movable portion in a displaced configuration.

FIG. 7E shows a schematic view of a flow regulating valve according to one form of the present technology.

FIG. 7F shows a schematic view of a flow regulating valve according to one form of the present technology, showing the movable portion in a deformed configuration and with an open entrainment port.

FIG. 7G shows a schematic view of a flow regulating valve according to one form of the present technology, comprising a spring coupled to the movable portion.

FIG. 7H shows a schematic view of a flow regulating valve according to one form of the present technology, comprising a spring coupled to the movable portion, wherein the movable portion is in a deformed configuration.

FIG. 7I shows a schematic view of a flow regulating valve according to one form of the present technology, comprising a spring and a damper coupled to the movable portion.

FIG. 7J shows a schematic view of a flow regulating vent arrangement according to one form of the present technology, comprising a flow regulating valve.

FIG. 7K shows a schematic view of another flow regulating vent arrangement according to one form of the present technology, comprising a flow regulating valve.

FIG. 7L shows a schematic view of the flow regulating vent arrangement shown in FIG. 7K, showing the movable portion in a deformed configuration.

Figure 8A:
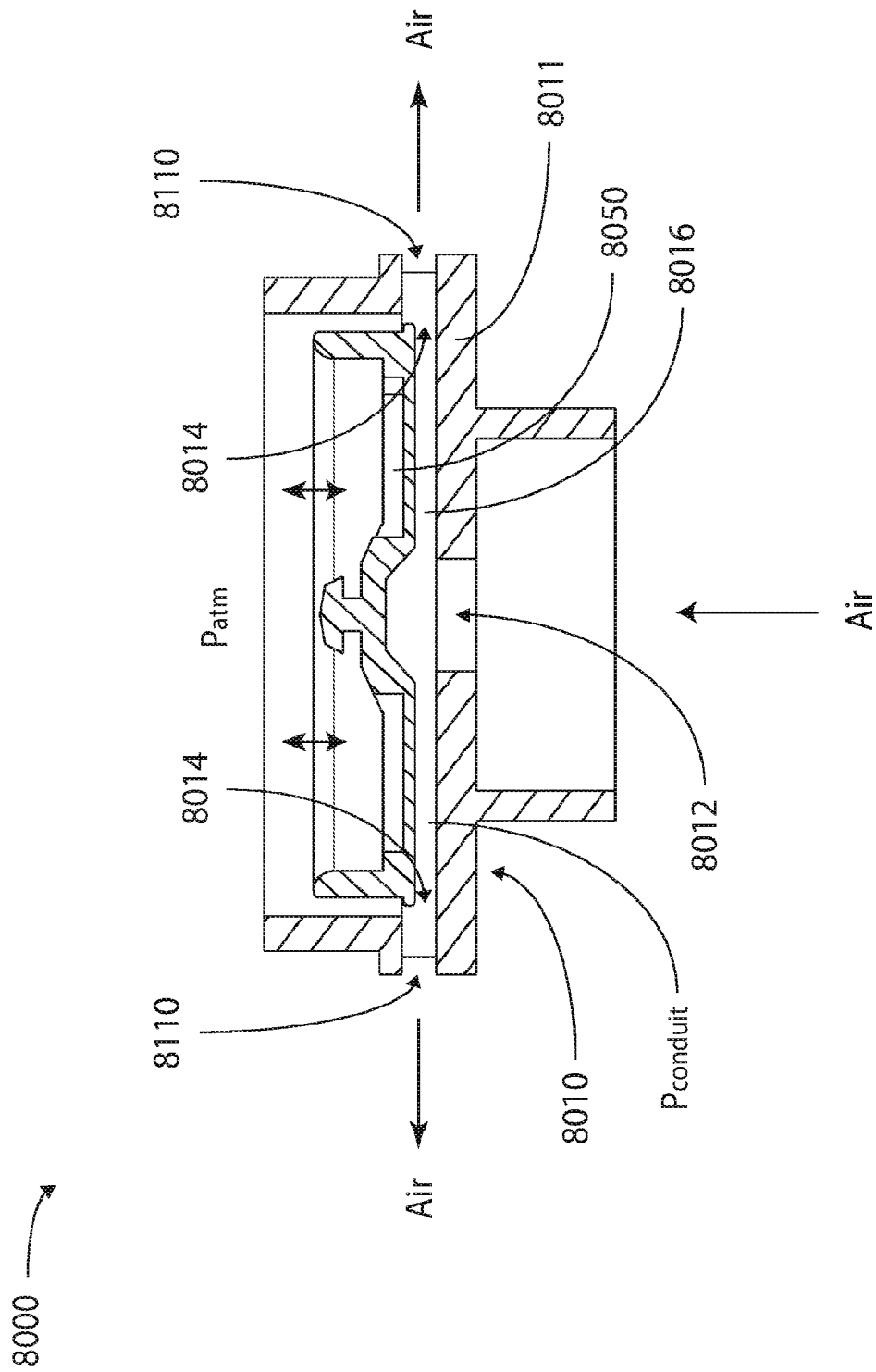

FIG. 8A shows a cross-section view of a flow regulating vent according to one form of the present technology.

Figure 8B:
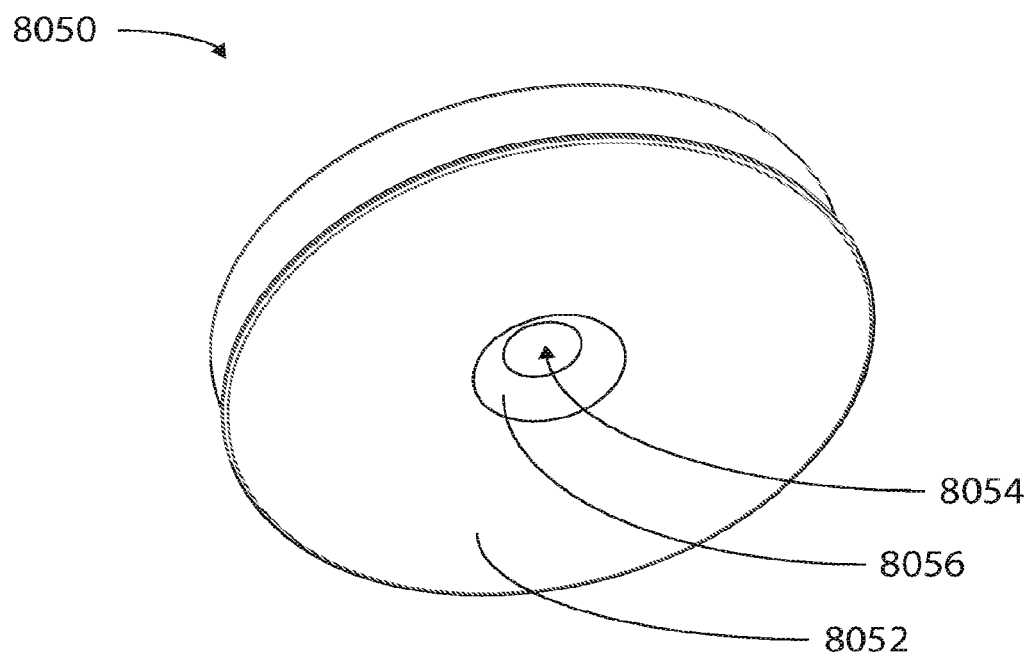

FIG. 8B shows a perspective view of a movable portion according to one form of the present technology.

Figure 8C:
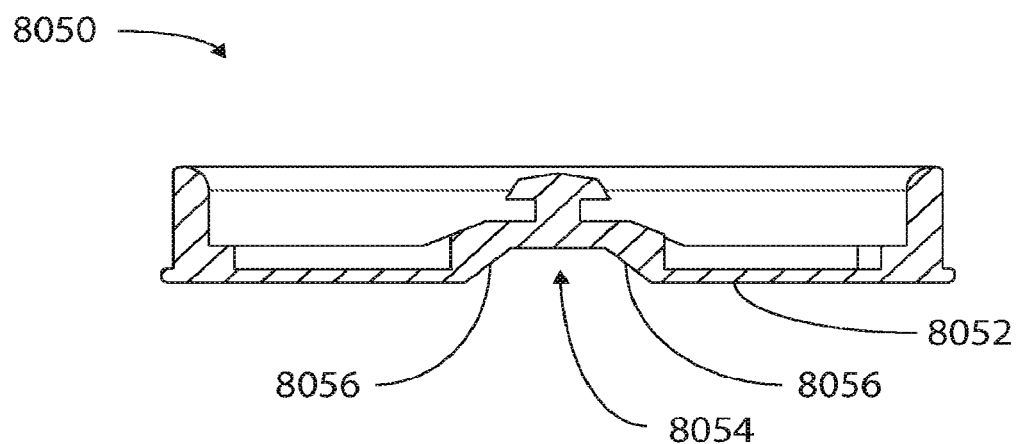

FIG. 8C shows a cross-section view of a movable portion according to one form of the present technology.

Figure 8D:
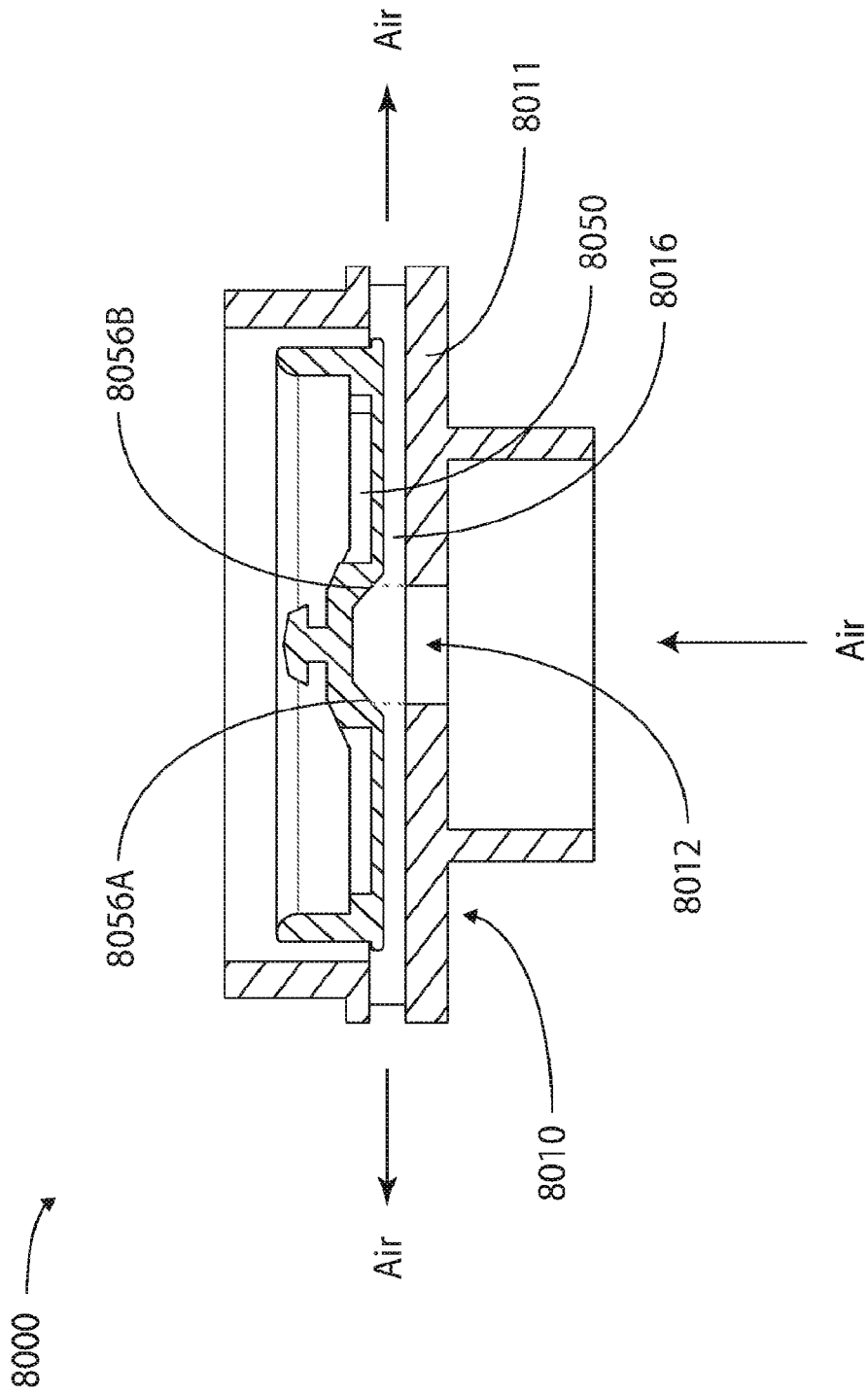

FIG. 8D shows a cross-section view of a flow regulating vent according to one form of the present technology.

Figure 8E:
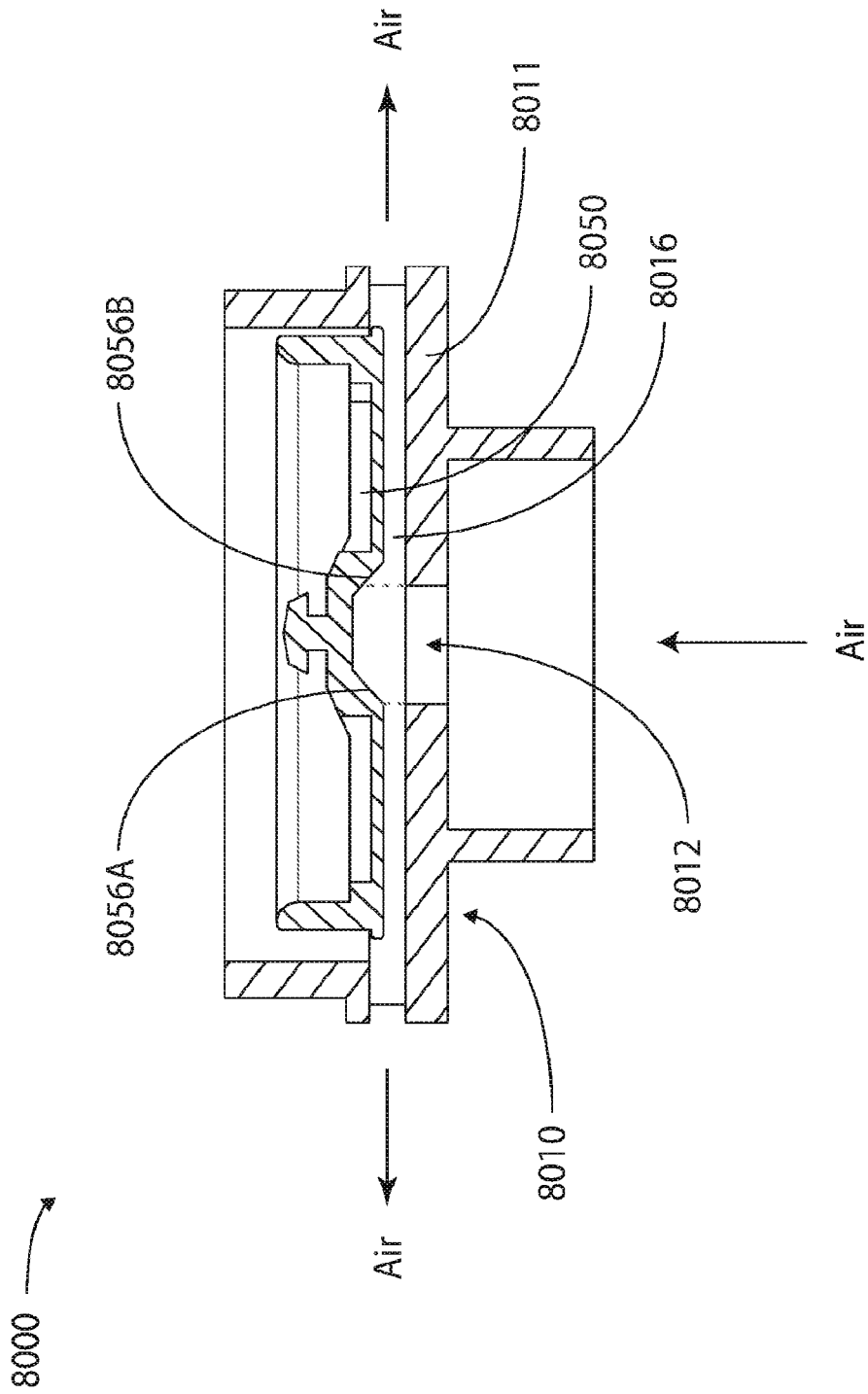

FIG. 8E shows a cross-section view of a flow regulating vent according to one form of the present technology, showing the movable portion to have moved to the right.

FIG. 8F shows a cross-section view of a flow regulating vent according to one form of the present technology, showing the movable portion to have moved to the left.

Figure 8G:
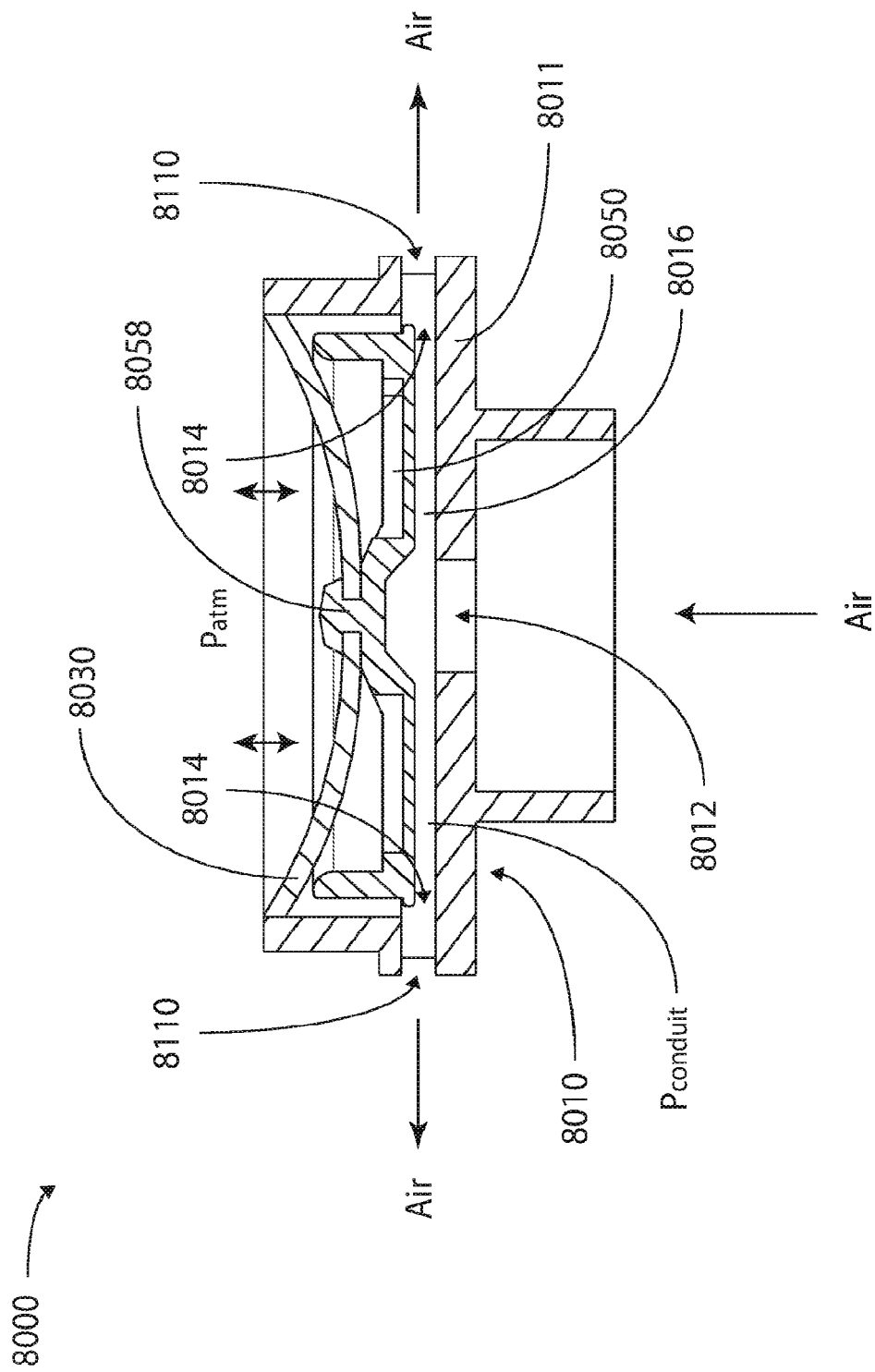

FIG. 8G shows a cross-section view of a flow regulating vent according to one form of the present technology, comprising a spring.

Figure 8H:
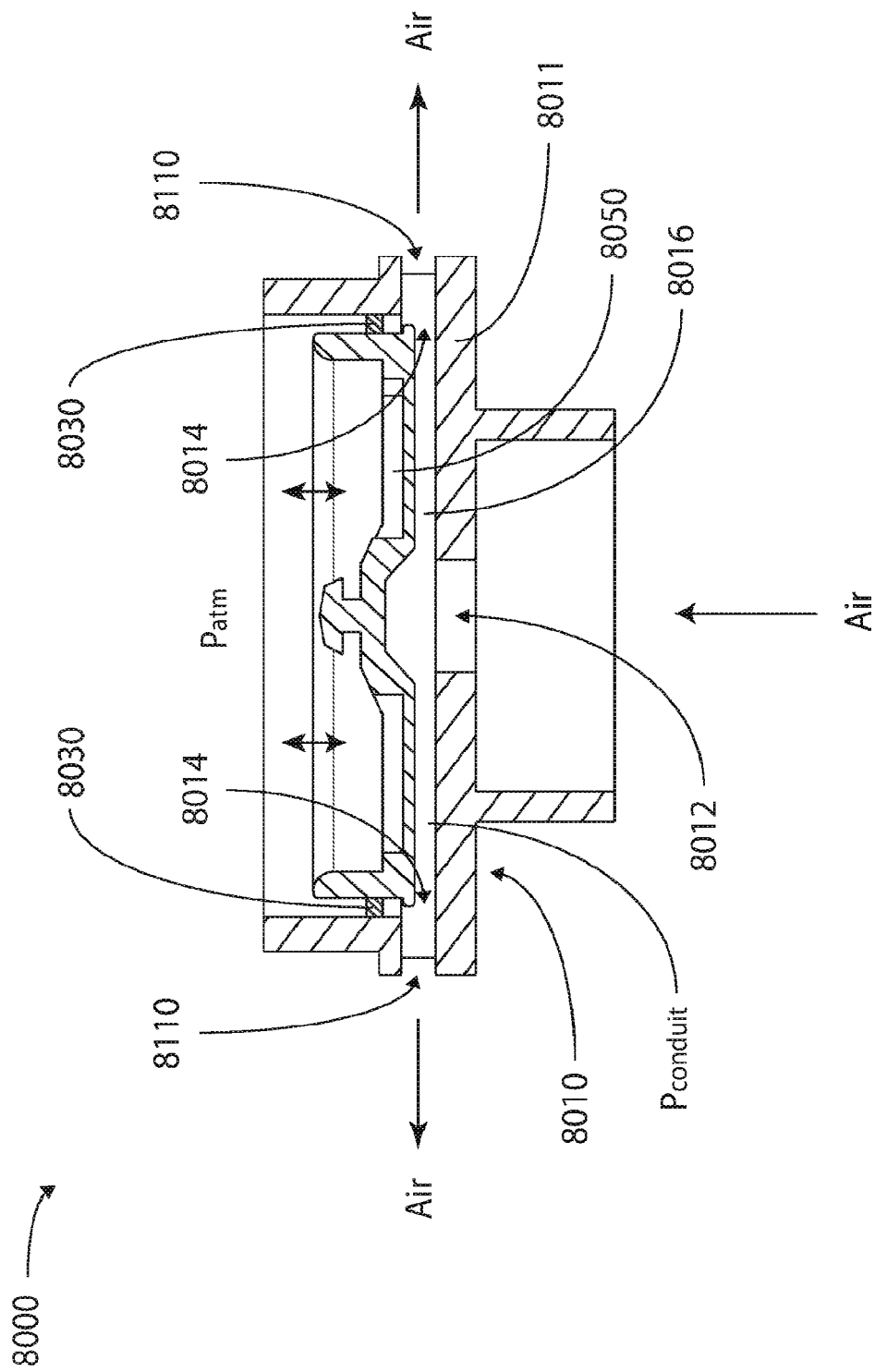
Figure 81:
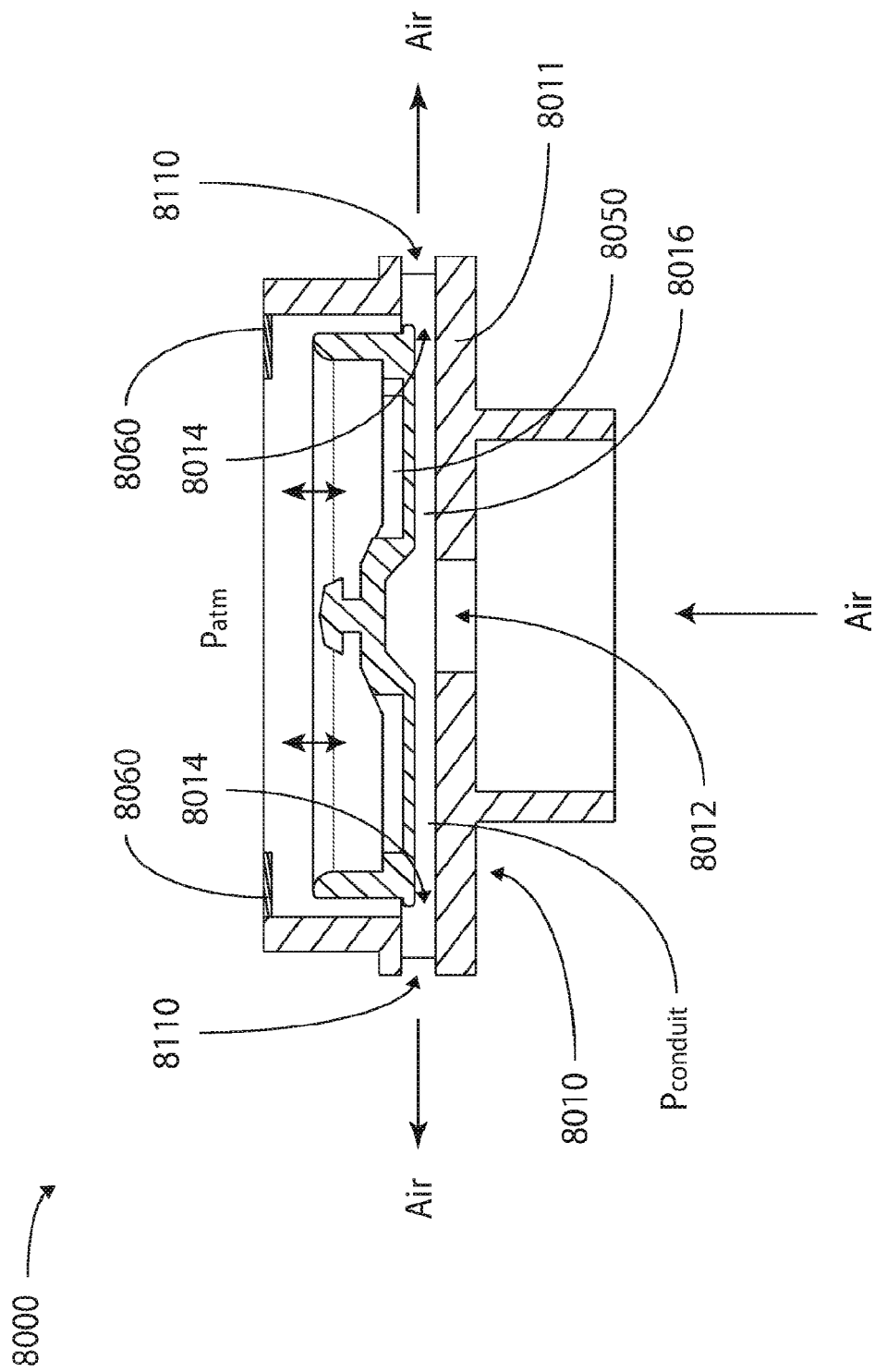

FIG. 8H shows a cross-section view of a flow regulating vent according to another form of the present technology, comprising a spring.

FIG. 8I shows a cross-section view of a flow regulating vent according to one form of the present technology, comprising a retaining flange.

Figure 8J:
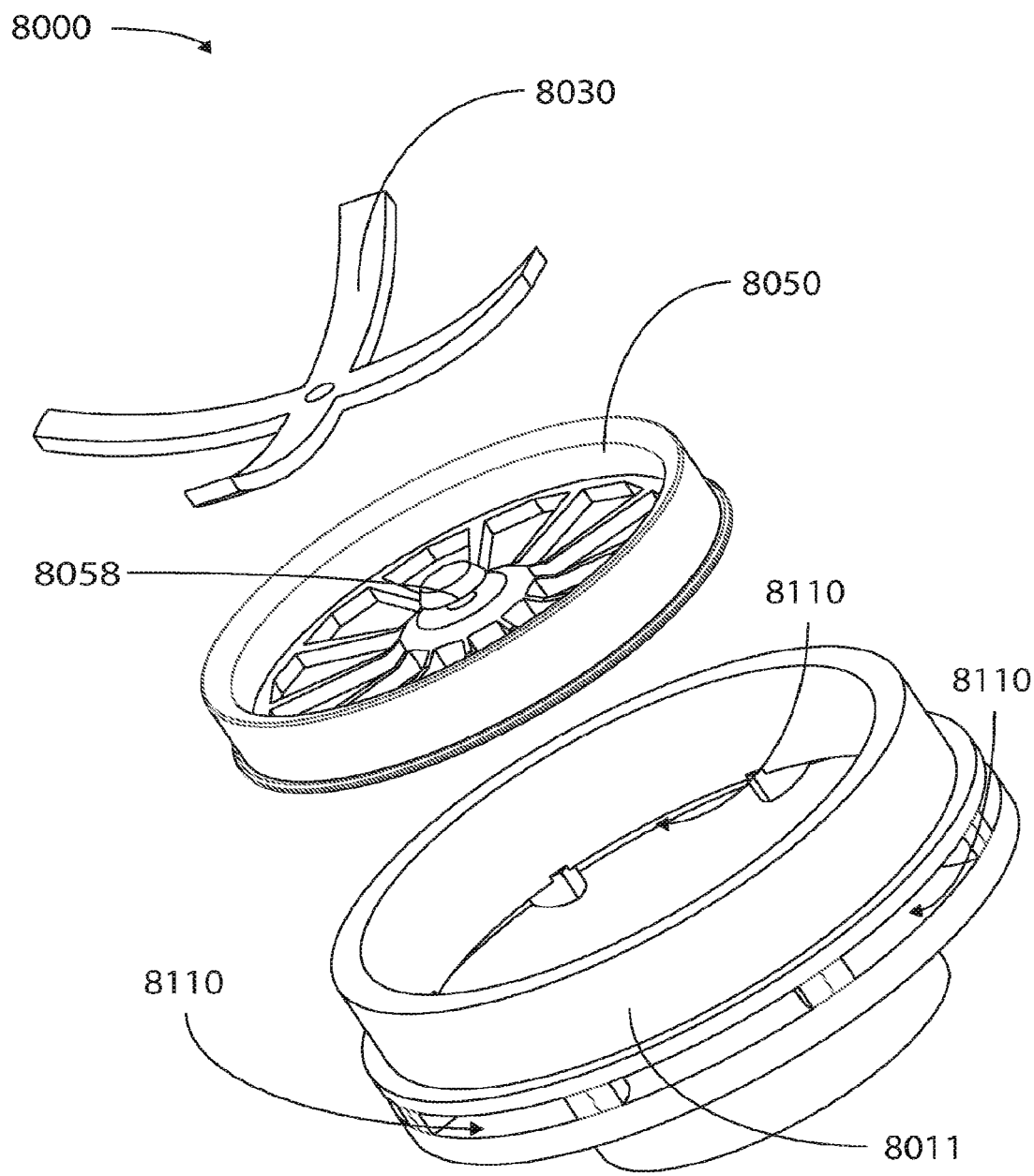

FIG. 8J shows an exploded perspective view of a flow regulating vent as shown in FIG. 8G.

Figure 8K:
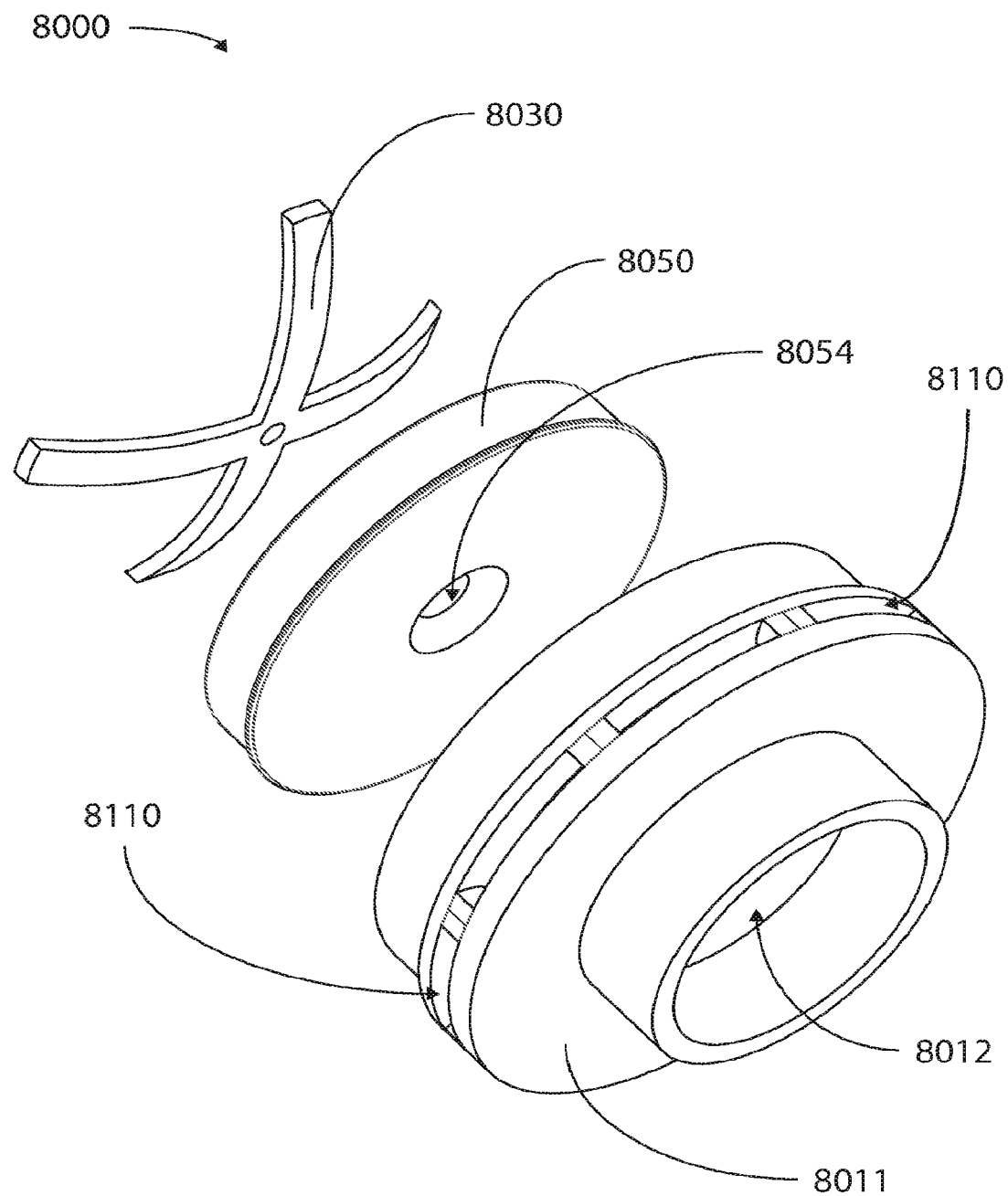

FIG. 8K shows another exploded perspective view of a flow regulating vent as shown in FIG. 8G.

Figure 8L:
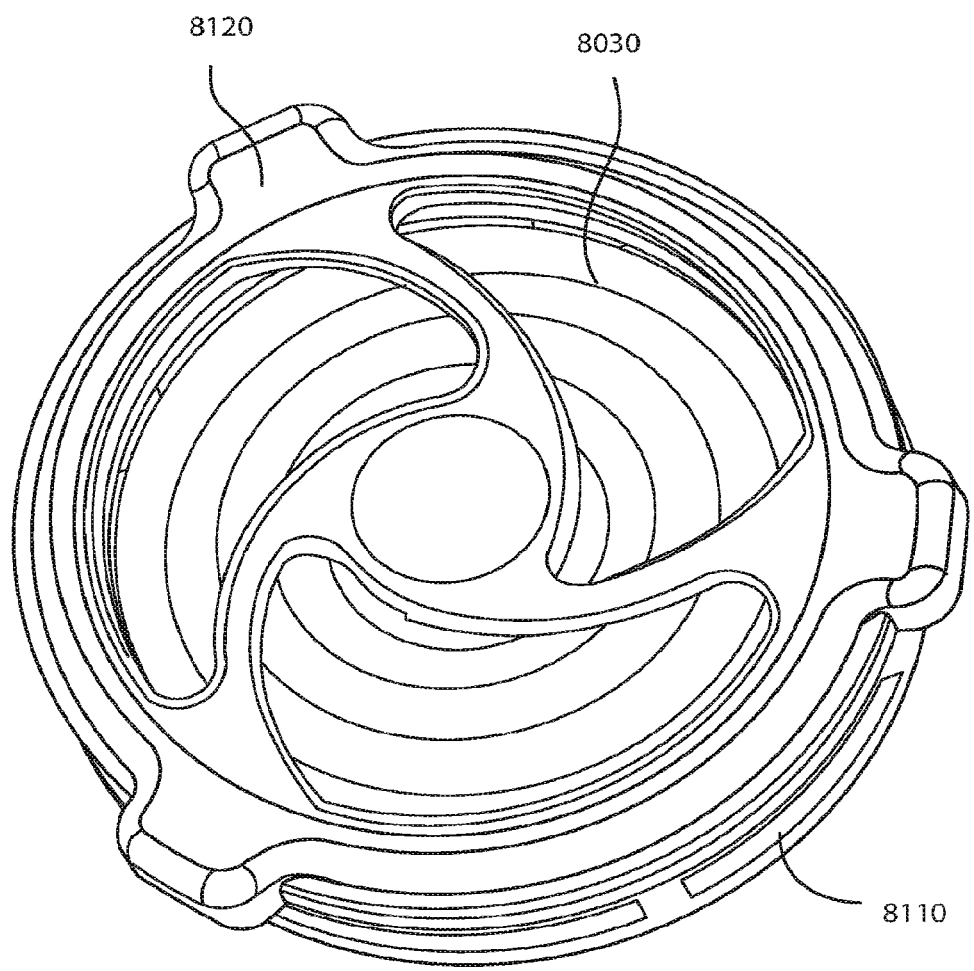

FIG. 8L shows a perspective view of a flow regulating vent according to one form of the present technology.

Figure 8M:
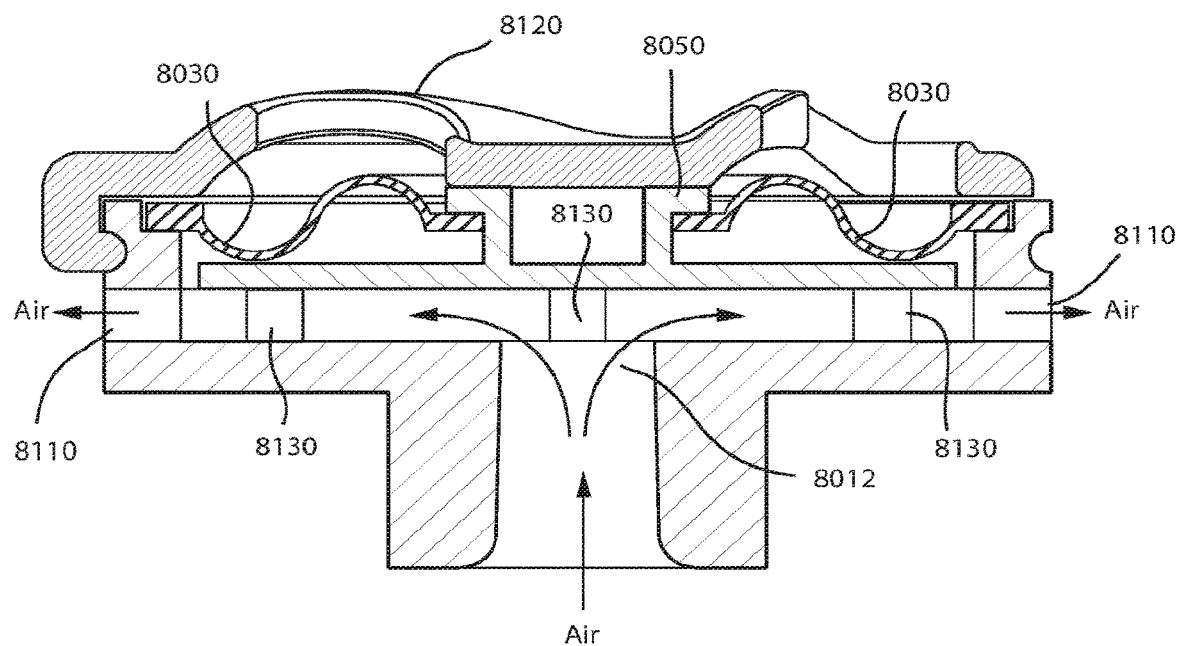

FIG. 8M shows a cross-section view of a flow regulating vent according to one form of the present technology with a single vent configuration.

Figure 8N:
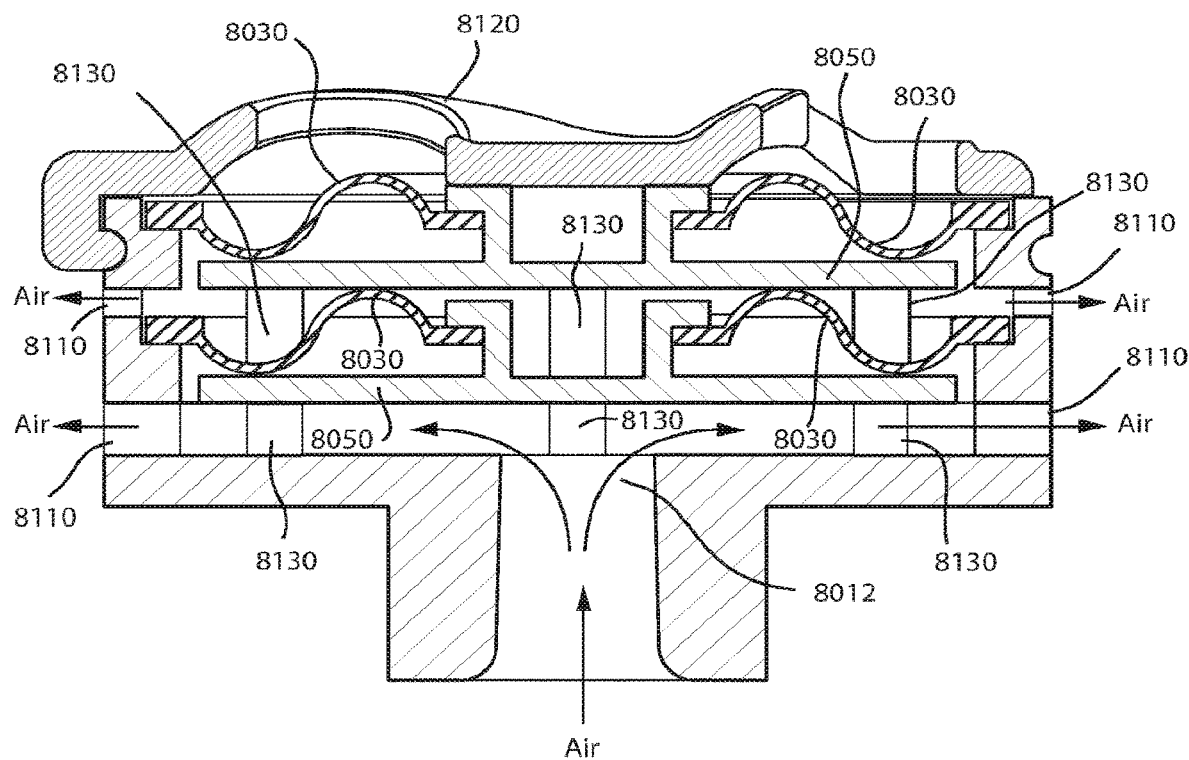

FIG. 8N shows a cross-section view of a flow regulating vent according to one form of the present technology with a double vent configuration.

Figure 8O:
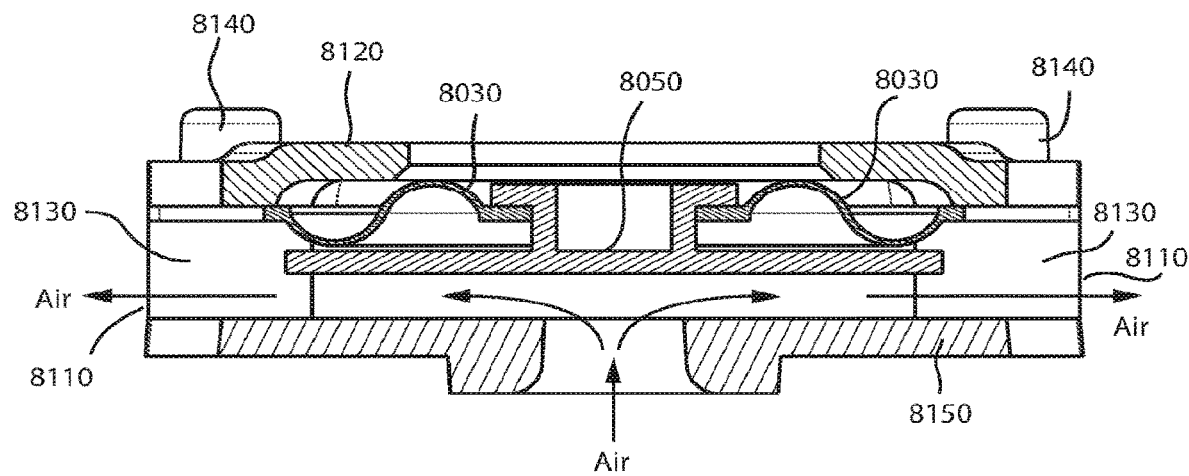

FIG. 8O shows a cross-section view of a flow regulating vent according to one form of the present technology.

Figure 8P:
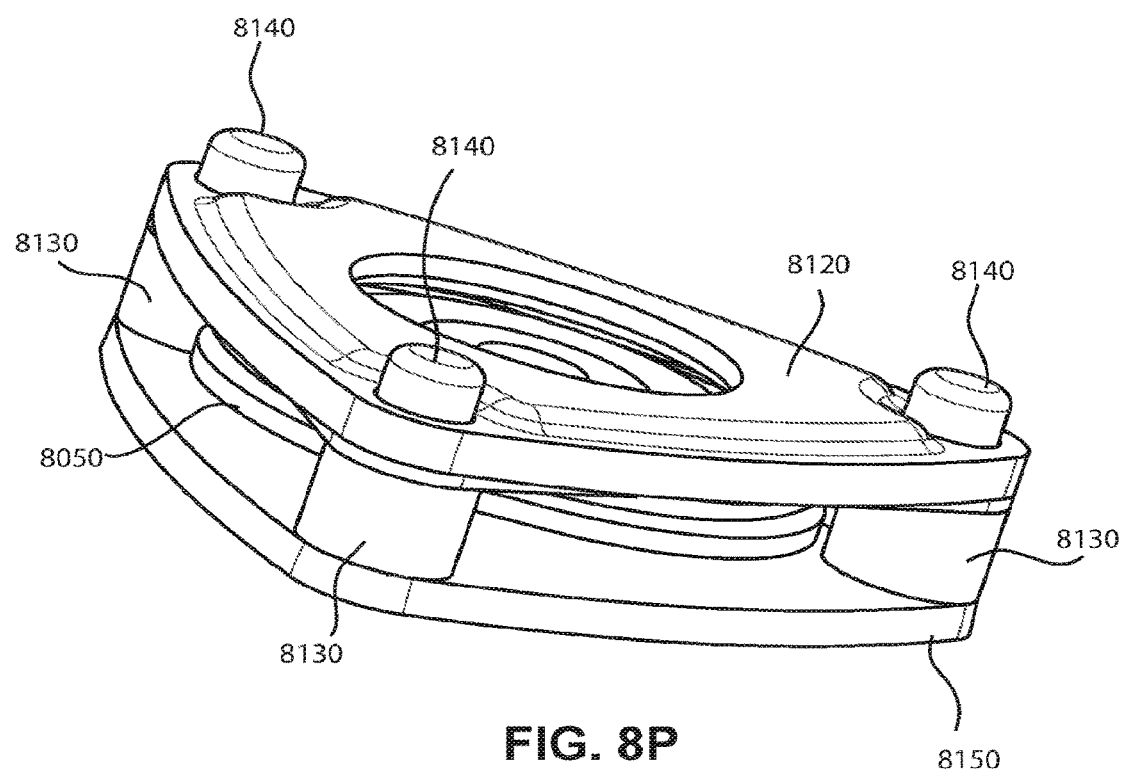

FIG. 8P shows a perspective view of the flow regulating vent of FIG. 8O.

Figure 8Q:
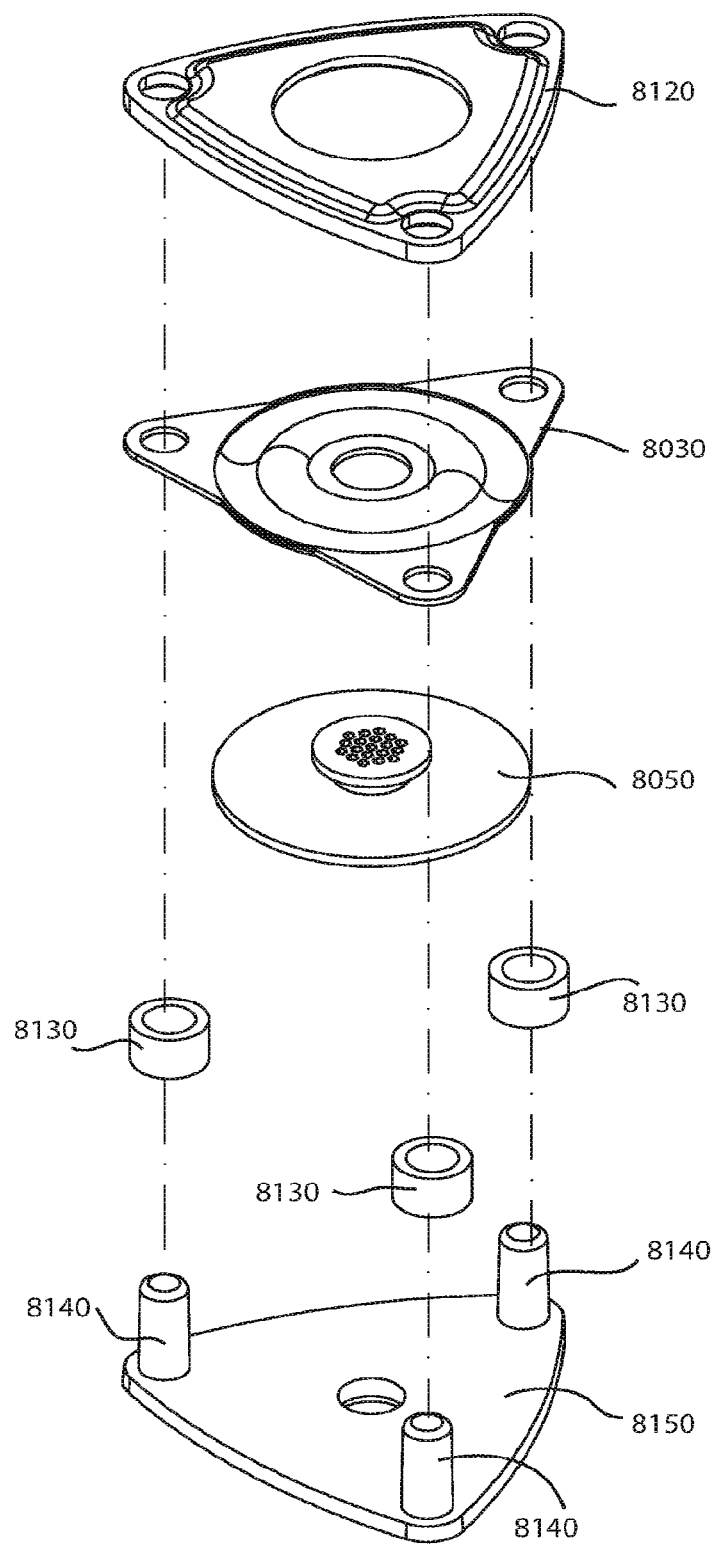

FIG. 8Q shows an exploded view of a flow regulating vent.

Figure 8R:
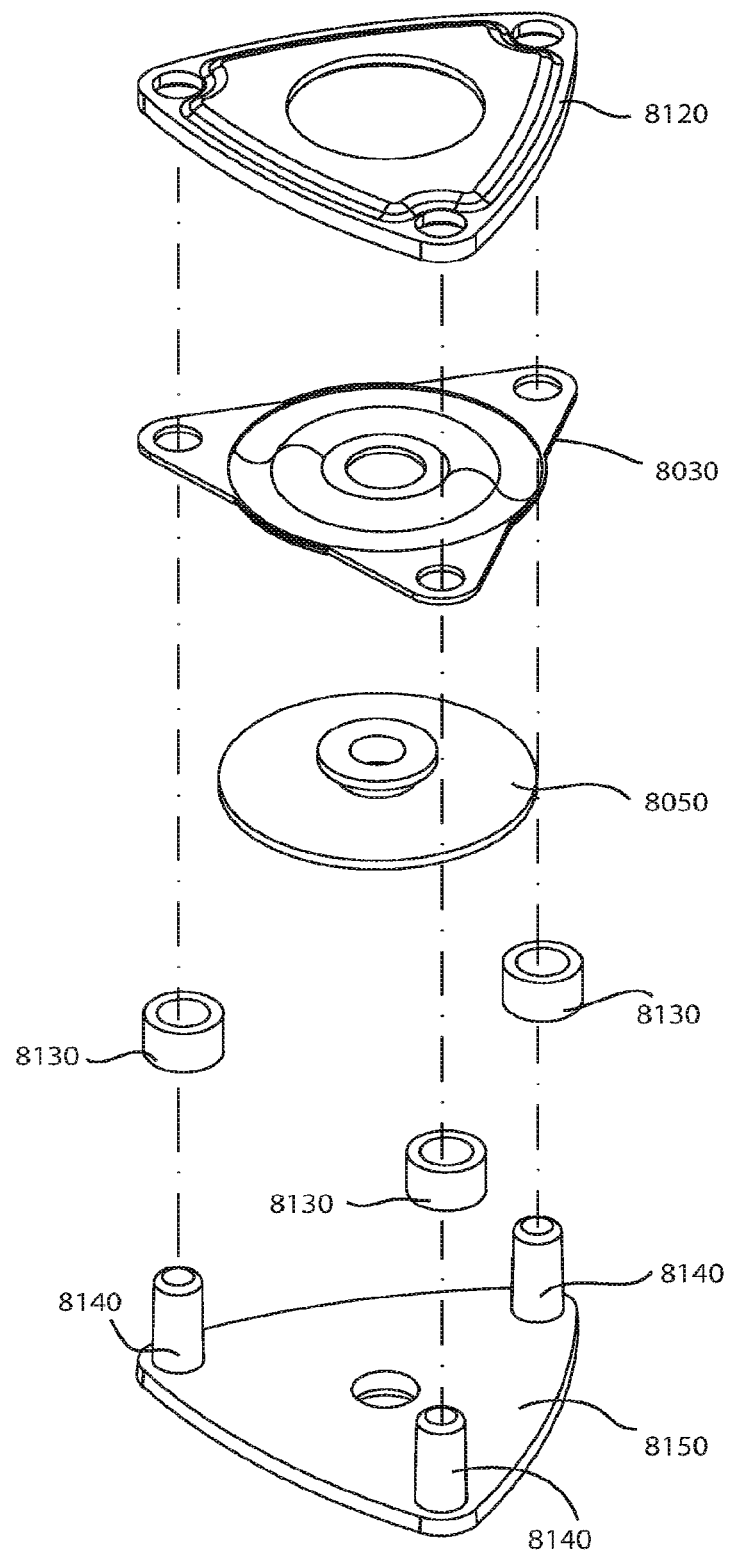

FIG. 8R shows an exploded view of a flow regulating vent.

Figure 9A:
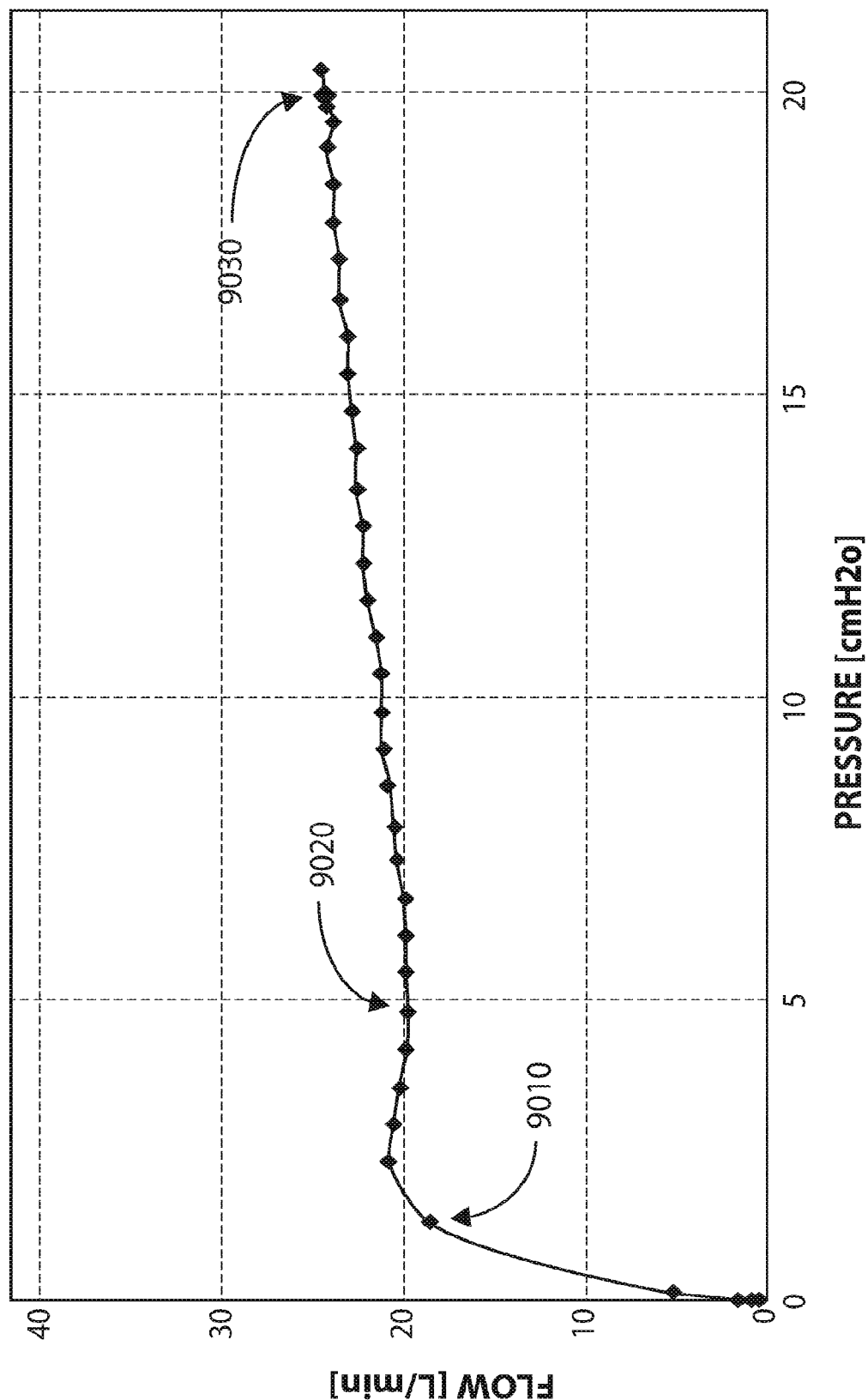

FIG. 9A shows an experimentally derived flow curve of a flow regulating vent according to one form of the present technology.

FIG. 9B shows an experimentally derived flow curve of another flow regulating vent according to one form of the present technology.

Figure 10:
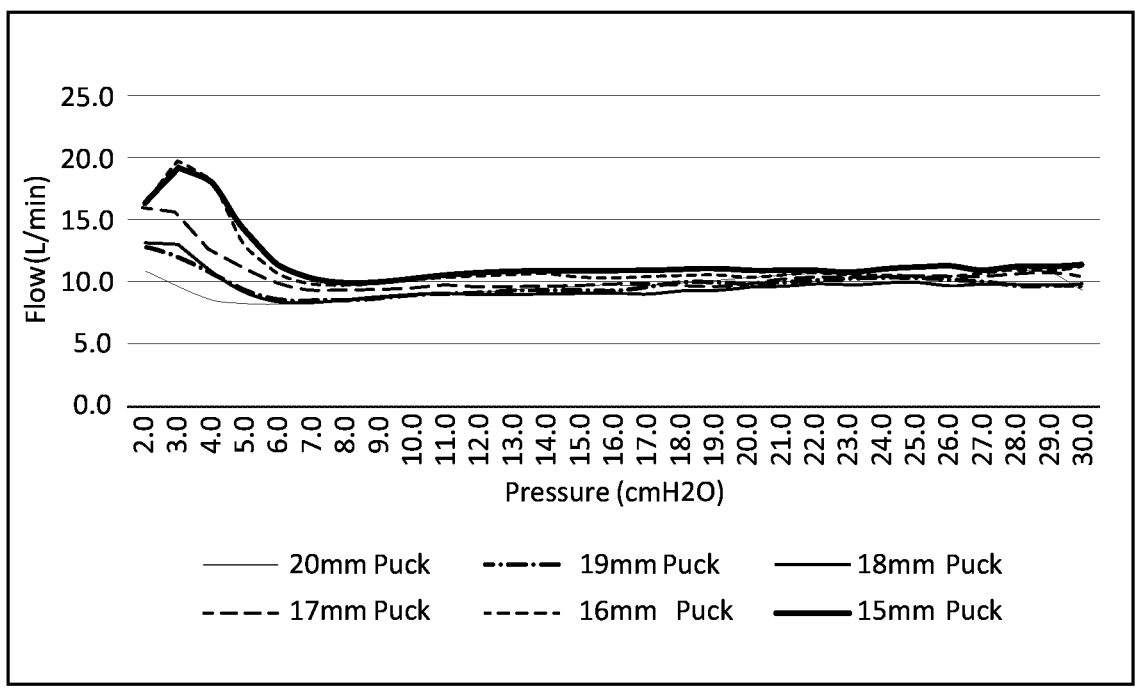

FIG. 10 is a graph that shows how adjusting the parameters of a vent arrangement affects gas flow.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 Patient Interface

Figure 3:
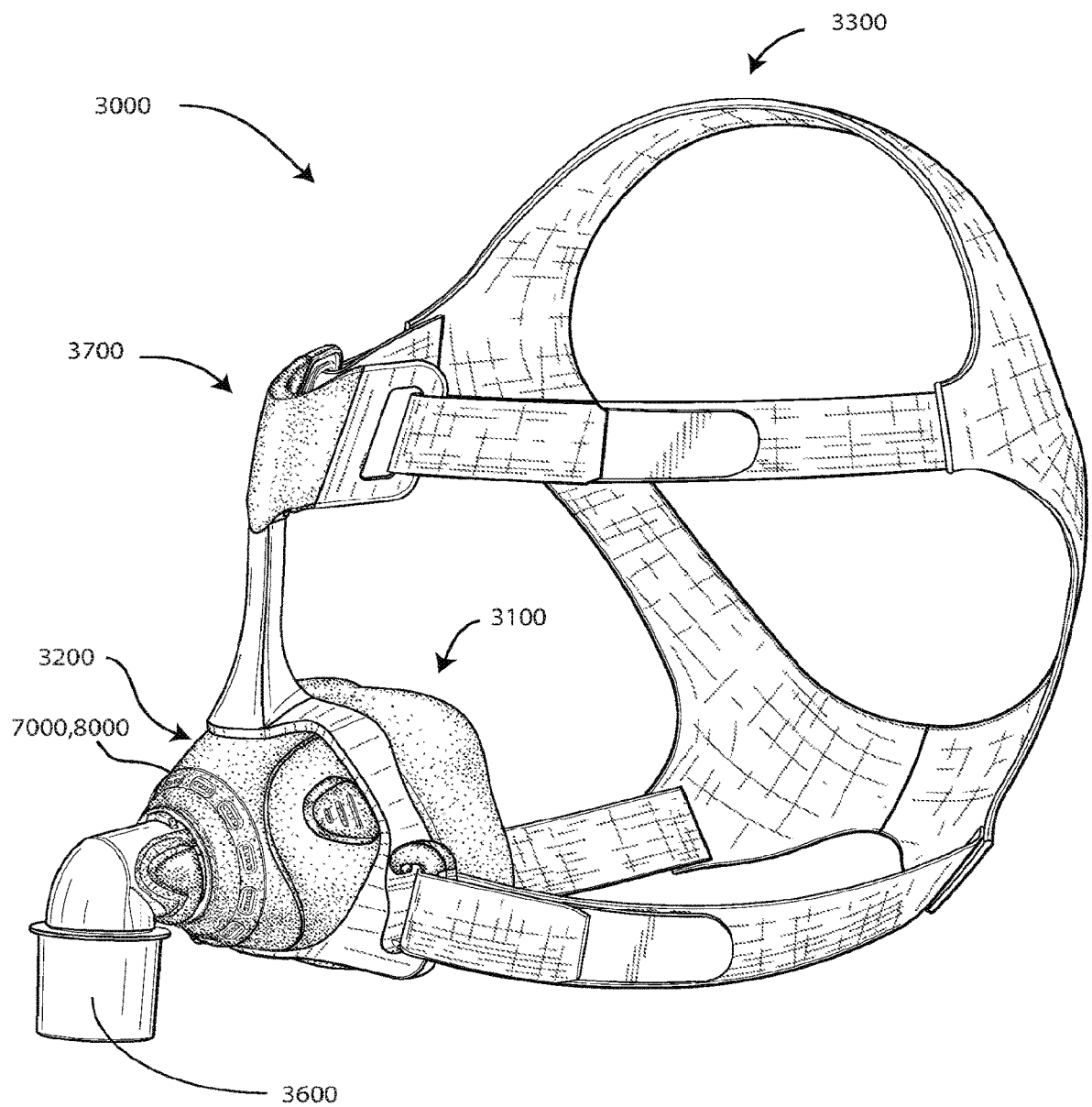
Figure 4A:
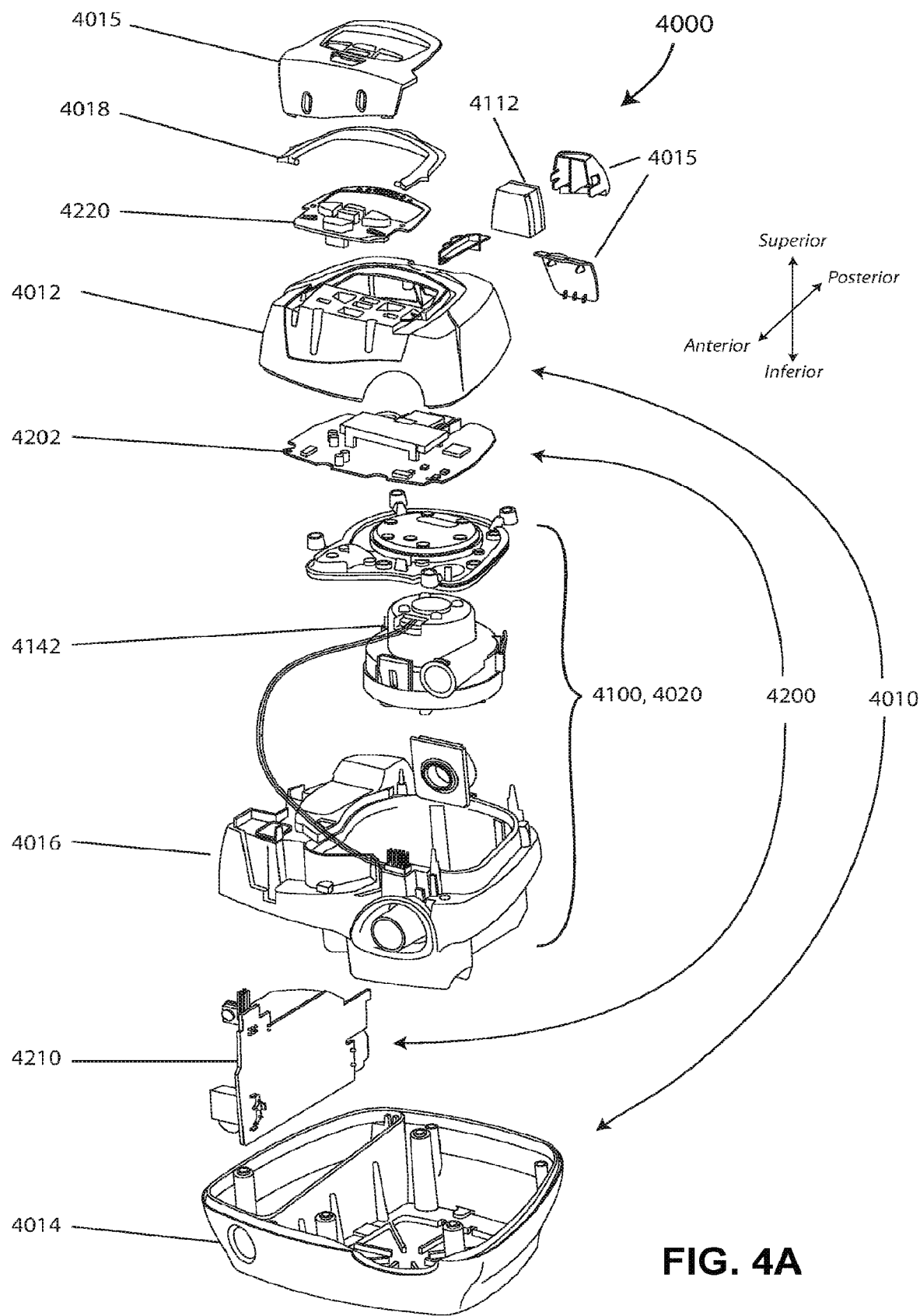
FIG. 4A shows an RPT device in accordance with one form of the present technology.
Figure 4B:
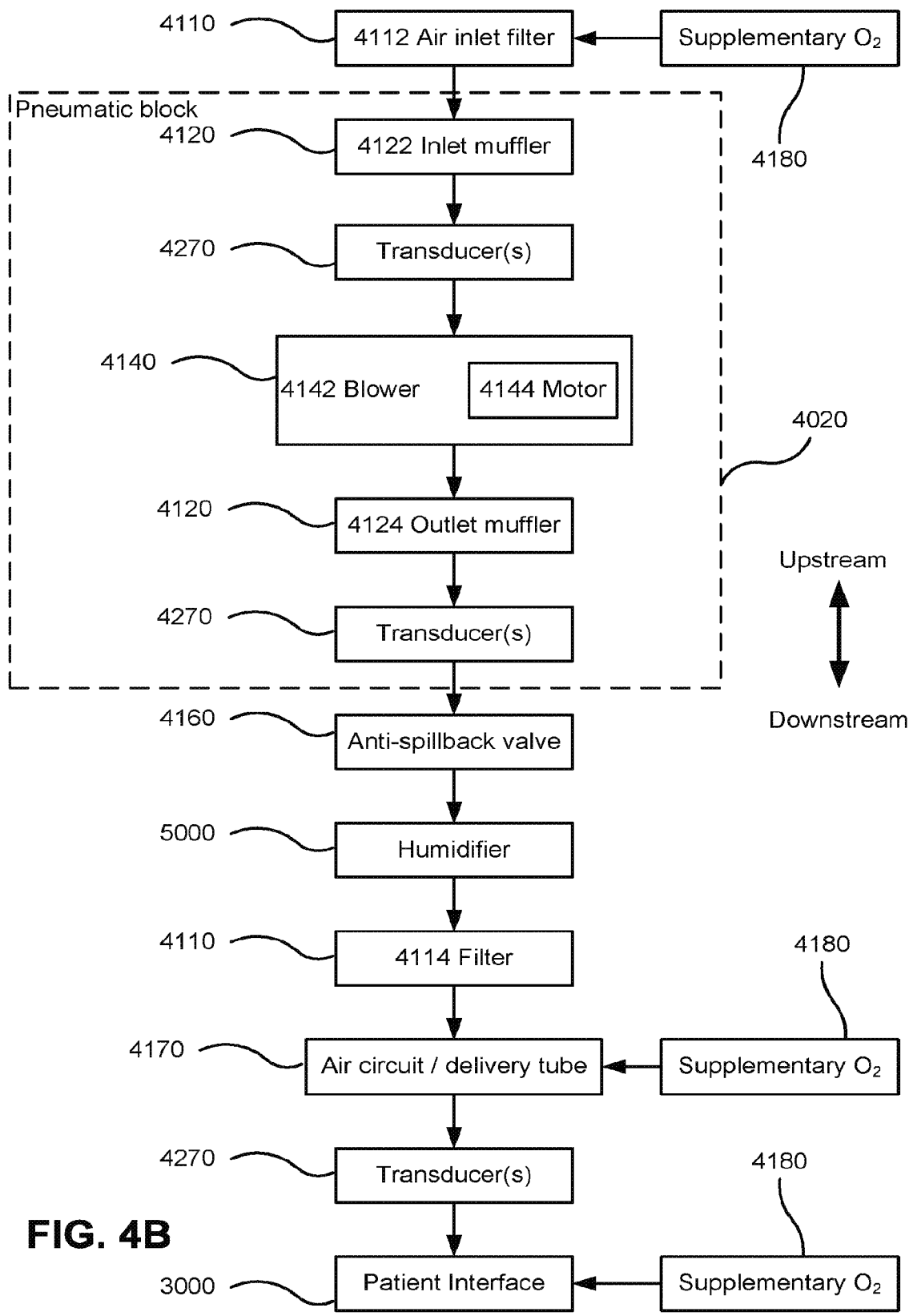
FIG. 4B is a schematic diagram of the pneumatic path of an RPT device in accordance with one form of the present technology. The directions of upstream and downstream are indicated.

A non-invasive patient interface 3000 in accordance with one aspect of the present technology is shown in FIG. 3. The exemplary patient interface 3000 comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

4.4 RPT Device

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Mechanical & Pneumatic Components

An RPT device may comprise one or more of the following components in an integral unit. In an alternative form, one or more of the following components may be located as respective separate units.

4.4.1.1 Pressure Generator

In one form of the present technology, a pressure generator 4140 for producing a flow, or a supply, of air at positive pressure is a controllable blower 4142.

4.4.1.2 Air Circuit

An air circuit 4170 in accordance with an aspect of the present technology is a conduit or a tube constructed and arranged to allow, in use, a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in United States Patent Application No. US/2011/0023874, which is incorporated herewithin in its entirety by reference.

4.5 Humidifier

4.5.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.6 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation about 7.5 L/minute. A typical duty cycle, the ratio of Ti to Ttot, is about 40%.

4.7 Vent/Valve Technologies

As will be described in further detail below, a vent may be located at one or more locations in the respiratory treatment system, including, but not limited to, a patient interface. For example, the vent may be located in the plenum chamber 3200, a mask wall, or an air delivery tube connecting member such as a swivel or an elbow. In addition, the vent may form a part of an air circuit and may form a part of an RPT device. It is contemplated that the vent may be a stand-alone component, for example, an in-line accessory. It is further contemplated that the treatment system may comprise a plurality of vents, such as one or more vents at each of one or more locations.

Each vent may be constructed and arranged to allow for the washout of exhaled gases, e.g. carbon dioxide. In accordance with the present technology, the vent may comprise one or more holes, for example, about 20 to about 80 holes, or about 40 to about 60 holes, or about 45 to about 55 holes.

A set of vents (i.e. one or more vents) in a respiratory treatment system may be referred to herewithin as a 'vent arrangement'. It is noted that 'a vent arrangement' may refer to the entirety of vents in a respiratory treatment system, or some of the vents (e.g. one, two or three vents) in a respiratory treatment system. A vent arrangement may of course comprise a plurality of components arranged to form an assembly.

A vent arrangement may comprise one or more of fixed orifice vent(s), variable orifice vent(s) and valve(s). For example, a fixed orifice vent comprising 20 holes and a valve fluidly connected upstream of the fixed orifice vent may be collectively referred to herein as a 'vent arrangement'. In another example, a vent arrangement may comprise a first fixed orifice vent comprising one hole and located in the patient interface, and a second fixed orifice vent comprising 20 holes and located in the air circuit. In a yet another example, a vent arrangement may comprise a fixed orifice vent comprising 30 holes and located in the patient interface.

4.7.1 Flow Regulating Valve

One aspect of the present technology relates to a valve. The valve may be a flow regulating valve, for example configured to regulate a flow rate of the gas flowing through a respiratory treatment system.

As previously described, it may be advantageous for a respiratory treatment system to be able to control (e.g. regulate to a range) a flow rate of gas flowing therethrough. The flow regulating valve in one form maintains a gas flow rate in a predetermined range across a range of pressures (e.g. differential pressures between the inlet and outlet of the flow regulating valve).

For example, assuming an outlet pressure of 0 cm $H_2O$ (i.e. atmospheric pressure), a flow regulating valve may be configured such that for an inlet pressure range of between 5 and 30 cm $H_2O$, the flow rate through the valve may be approximately between 20 and 25 L/min. In another example, a flow regulating valve may be configured such that for an inlet pressure range of between 10 and 20 cm $H_2O$, the flow rate through the valve may be approximately between 17 and 20 L/min.

The preferred range of flow rate(s) through the valve and their relationships to pressures (e.g. inlet pressures and/or differential pressures) may depend on a number of factors, such as a type of therapy and a patient.

FIG. 7A shows a schematic representation of a flow regulating valve 7010 according to one aspect of the present technology. The flow regulating valve may comprise an inlet 7012 and an outlet 7014, and a variable conduit 7016 through which the gas flow travels. The variable conduit 7016 may deliver the flow of gas from the inlet to the outlet. The variable conduit 7016 may comprise a movable portion 7050 configured to move to change an impedance of the variable conduit. An impedance of a variable conduit may be increased by for example decreasing a size of its cross section for the flow to travel therethrough. Conversely, increasing a size of a cross section may decrease an impedance. In some forms, a change in a shape of a cross section may increase or decrease its impedance.

It will be understood that, typically, discussions in regards to cross sections for flows of air therethrough relate to cross sections with a normal coincident with a direction of the flow of air.

The movable portion 7050 may comprise a first side and a second side. The movable portion 7050 may move (e.g. displace and/or deform) according to air pressures of the first side and the second side. In one form, the first side of the movable portion may be exposed to the gas flow to be regulated (e.g. the first side may be a part of the variable conduit as shown in FIG. 7A), and the second side of the movable portion may be exposed to another, reference pressure (e.g. the second side may be located in ambient air as shown in FIG. 7A). It will be understood that other configurations of the movable portion 7050 may be also suitable while remaining within the scope of the present technology.

The movable portion 7050 may be configured to deform, e.g. from a straight configuration as shown in FIG. 7A to that shown in FIG. 7B. Additionally, or alternatively, the movable portion 7050 may be configured to displace, e.g. from a first position as shown in FIG. 7C to that shown in FIG. 7D. Thus, the movable portion 7050 may move between a first configuration and a second configuration to change an impedance of the variable conduit 7016.

In some configurations, the movable portion 7050 may be configured to displace and deform. For example, a first portion of the movable portion 7050 may deform while a second portion of the movable portion 7050 may displace. In another example, one portion of the movable portion 7050 may both deform and displace between a first configuration and a second configuration.

It is also contemplated that a flow regulating valve may comprise a plurality of movable portions in some forms.

The movement of the movable portion 7050 may change a configuration of the variable conduit 7016. For example, the variable conduit 7016 may comprise an increased impedance in configurations shown in FIG. 7B and FIG. 7D in comparison to configurations shown in FIG. 7A and FIG. 7C respectively.

It is contemplated that the variable conduit 7016 may be configured in one of a number of suitable forms for allowing fluid communication between the inlet and the outlet with variable impedance. For example, the variable conduit 7016 may comprise a rectangular cross section, an oval cross section, or a circular cross section. In another example, the variable conduit 7016 may comprise a plurality of pathways for fluid to travel therethrough. In some forms, the variable conduit 7016 may comprise a plurality of cross sections, for example varying across its length, and/or varying between a plurality of pathways in the conduit.

The movable portion 7050 may thus be configured such that it may move based on the ambient pressure ($P_{atm}$) and the air pressure in the variable conduit ($P_{conduit}$). For instance, in the arrangement shown in FIG. 7A, the ambient pressure ($P_{atm}$) and the air pressure in the variable conduit ($P_{conduit}$) may be substantially equal, whereby the movable portion 7050 remains unbiased. In another arrangement, shown in FIG. 7B, the ambient pressure ($P_{atm}$) may exceed the air pressure in the variable conduit ($P_{conduit}$) such that the movable portion 7050 is biased inwards, reducing a size of the variable conduit 7016.

It will be understood that an increase in air velocity may cause a decrease in pressure (Bernoulli's principle). Therefore, if a velocity of the air flow through a conduit (e.g. variable conduit 7016 shown in FIG. 7A and FIG. 7B) is changed, the corresponding pressure of the air flow may be changed in turn. Accordingly, the change in air pressure in the variable conduit ($P_{conduit}$) may change a size (e.g. width $W_{conduit}$) of the variable conduit. Furthermore, the change in size (e.g. width $W_{conduit}$) of the variable conduit may affect the velocity of the air ($V_{air}$) therethrough.

Thus, a change to one or more of the velocity of the air ($V_{air}$), air pressure in the variable conduit ($P_{conduit}$) and size of the variable conduit ($W_{conduit}$) affect each other, until equilibrium is reached.

For example, an increase in a velocity of the air flow through the variable conduit 7016 from a configuration shown in FIG. 7A may reduce the corresponding pressure of the air flow. Accordingly, the reduction in air pressure in the variable conduit ($P_{conduit}$) may reduce a size (e.g. width $W_{conduit}$) of the variable conduit, such as to a configuration shown in FIG. 7B. The flow regulating valve 7010 thereby reduces the velocity of the air ($V_{air}$) therethrough and regulates the volume flow rate of air.

As it relates to a respiratory treatment system, a flow rate of air through one or more portions of the respiratory treatment system may vary throughout its operation. One such example may be a variation of flow rates between an inspiratory phase and an expiratory phase of a patient. An exemplary patient waveform is shown in FIG. 6, and shows variations in patient flow rates throughout a breath. As described above, a typical peak inspiratory flow rate may be 0.4 L/s and a typical peak expiratory flow rate may be approximately −0.5 L/s.

Thus, a variation between a peak inspiratory flow rate and a peak expiratory flow rate may be approximately 0.9 L/s, or 54 L/min. These variations in patient flow rates may cause variations in flow rates of the respiratory treatment system.

Figure 1:
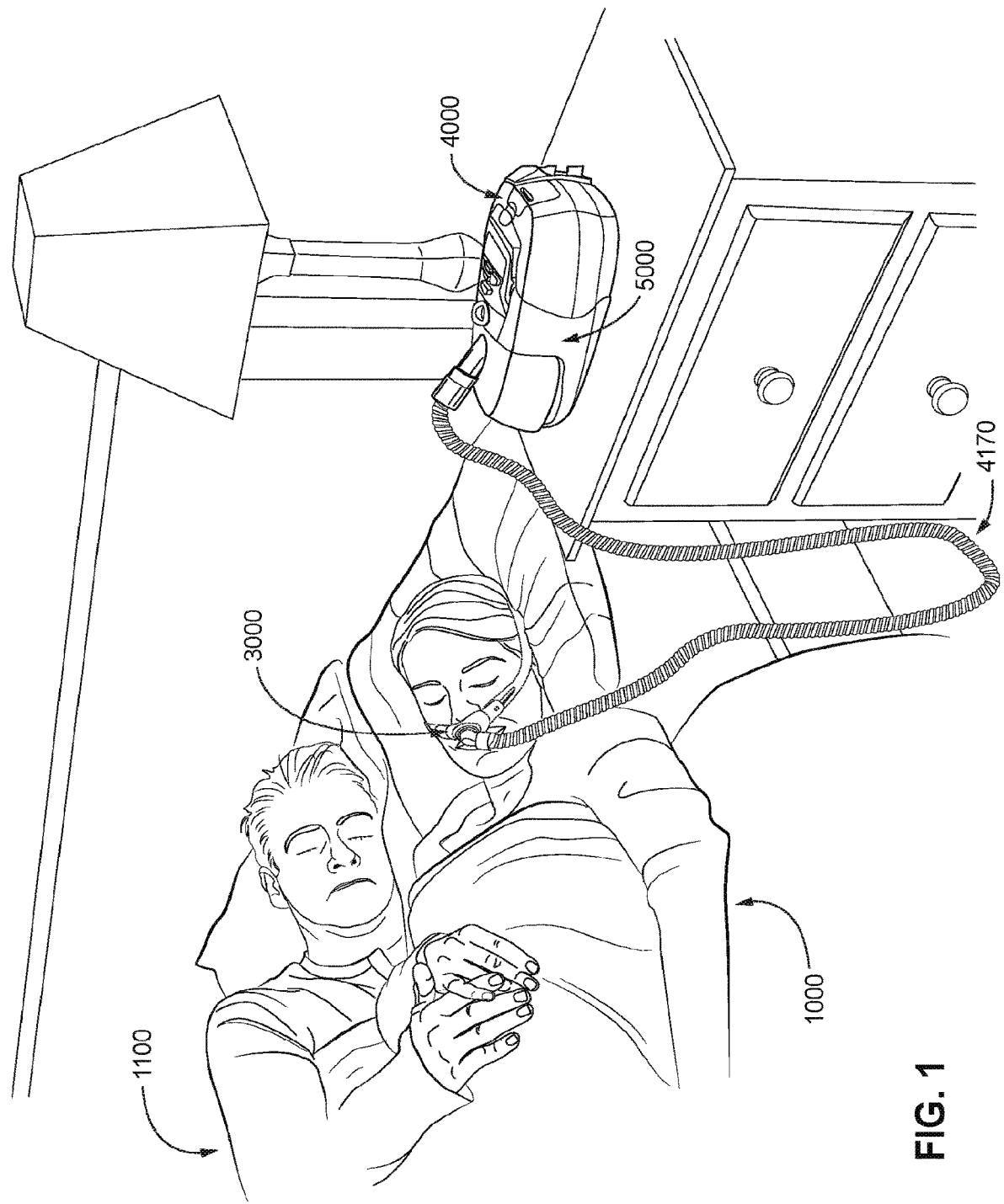
Figure 2:
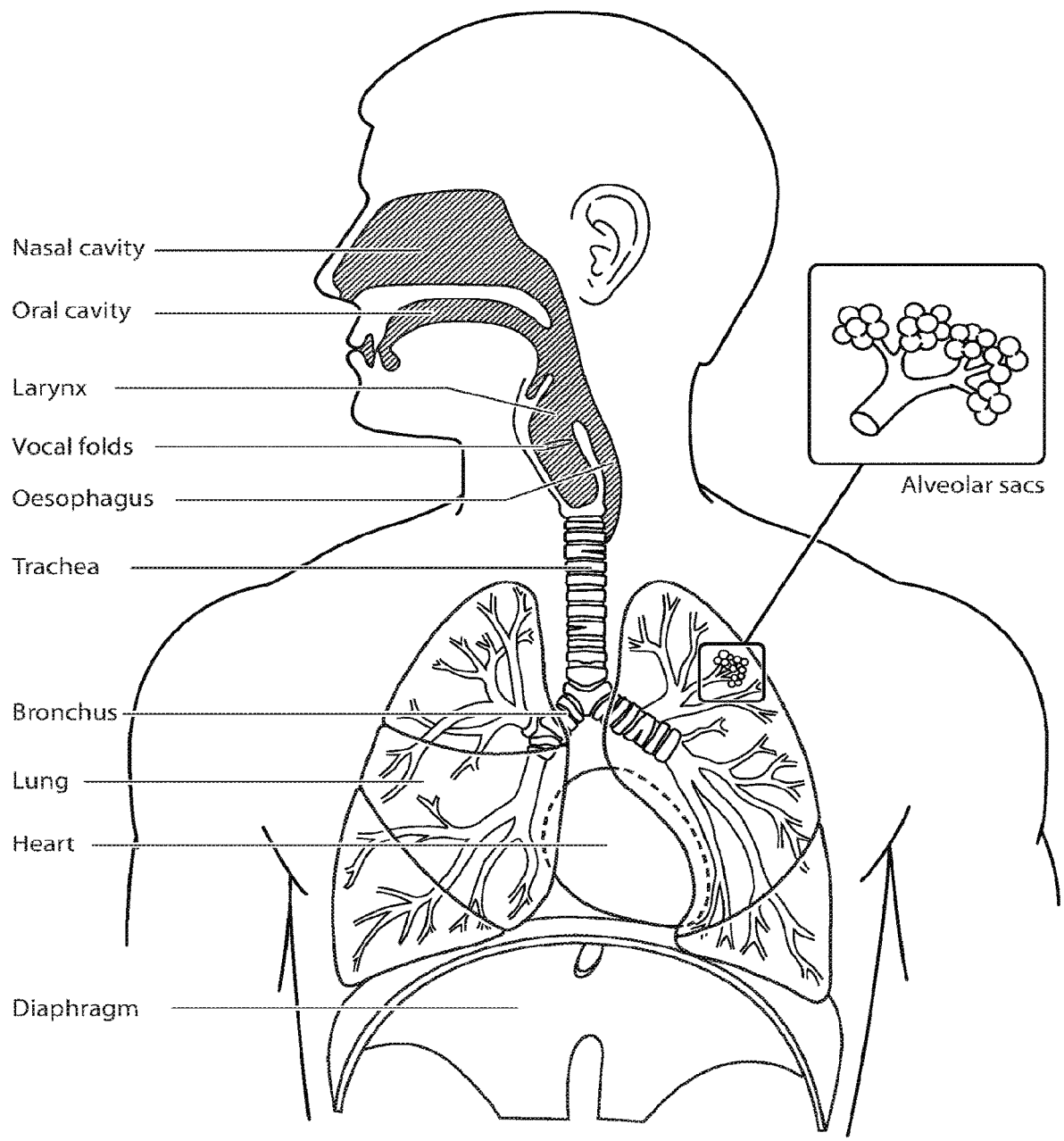

In a respiratory treatment system such as that shown in FIG. 1, a flow rate of air through an air circuit 4170 connecting the RPT device 4000 to a patient interface 3000 may increase during inspiration of a patient 1000, and decrease during expiration of a patient 1000. In a similar system, a flow rate of air being washed out through a vent arrangement in the patient interface 3000 may increase during an expiration of the patient while decreasing during an inspiration of the patient.

In a respiratory treatment system, the total energy in the flow of air may remain substantially identical during inspiration and expiration of a patient. Thus, an increase in the velocity (i.e. volume flow rate) of the flow of air would cause a decrease in pressure. As a result, a flow regulating valve 7010 may be configured such that an increase in the flow of air may be regulated by a change in size of the variable conduit 7016.

In a respiratory treatment system wherein its vent arrangement consists of fixed orifice vents, a flow rate through the vent arrangement may increase significantly as a treatment pressure increases. However, in some cases, an excessively high flow rate may lead to wastage of power, air, and/or oxygen, and potentially lead to higher noises and disturbances to the patient and/or a bed partner.

Advantageously, the flow regulating valve 7010 may thus be configured to regulate a flow rate of air. For example a flow regulating valve 7010 may be used to reduce a rate of increase of the flow rate through a vent arrangement as a function of operating pressure, such as in comparison to a fixed orifice vent. In another example, a flow regulating valve 7010 may be used to substantially eliminate a variation in flow rates across a range of operating pressures.

The flow regulating valve 7010 according to some aspects of the present technology may exhibit favourable characteristics in terms of noise. Not only does a regulation of a flow rate itself reduce noise outputs, the inventors have determined that particular aspects of the flow regulating valve 7010 lead to improved noise outputs. In some prior art flow regulating valves, a localised high air velocity or a shutting of an orifice may cause unwanted noise. Advantageously, the flow regulating valve 7010 may be configured such that the flow rate of air is regulated, while maintaining a substantially even distribution of air flow therethrough.

The flow regulating valve 7010 according to some forms of the present technology may evenly distribute the air flow therethrough while regulating the rate of air flow travelling therethrough.

In some forms of the present technology, the flow regulating valve 7010 may comprise an entrainment orifice 7020.

The entrainment orifice 7020 may be always open (e.g. a fixed orifice), or may be selectively opened for example according to a movement of the movable portion 7050.

In one form, the entrainment orifice 7020 may be closed while the movable portion 7050 is in a first position (e.g. as shown in FIG. 7E). The entrainment orifice 7020 may for example open when the movable portion 7050 is in a second position, such as constricting the variable conduit 7016 (e.g. as shown in FIG. 7F), thereby drawing in additional air from the atmosphere.

4.7.1.1 Biasing

The flow regulating valve may comprise a biasing mechanism such as a spring according to some forms of the present technology.

The biasing mechanism may provide and/or adjust (e.g. increase) a threshold above which the movable portion 7050 may be moved. For example, the biasing mechanism may comprise a magnet, or a pre-loaded (pre-tensioned or pre-compressed) spring holding the movable portion 7050 in place, such as at a first force. In such an arrangement, movable portion 7050 may not begin to move from its first configuration (e.g. variable conduit 7016 in a fully open position) until the first force (e.g. of the spring or the magnet) is overcome.

Additionally, or alternatively, the biasing mechanism may provide and/or adjust (e.g. increase) a rate of movement of the movable portion 7050 in relation to the pressures acting on the movable portion. The biasing mechanism may thus provide and/or adjust a spring rate of the movable portion 7050. In one example, a spring 7030 may be coupled to the movable portion, such that a movement of the movable portion may require an extension of the spring 7030, as shown in FIG. 7G and FIG. 7H.

The biasing mechanism may be variably configured.

In some forms, the biasing mechanism may comprise a non-linear spring rate, such as an increasing, or a decreasing spring rate, for example as a function of valve position. A flow regulating valve comprising a biasing mechanism with a variable spring rate may thus behave in a non-linear fashion, such as at various points of operation of the valve (e.g. according to an increasing pressure).

In some forms, the biasing mechanism may comprise an adjustable spring rate. The spring rate may be adjusted by one or more of: an interchangeable component, a mechanically adjustable spring or an electro-mechanical spring and any other known methods.

The biasing mechanism may also be used to reduce an effect of orientation of the flow regulating valve 7010 on its operation. A change in orientation of the flow regulating valve 7010 may change the direction of gravity acting on the movable portion 7050 in relation to the flow regulating valve 7010. Therefore, use of a biasing mechanism to adjust a pre-load the movable portion 7050 may reduce an effect of a change in orientation.

For example, if a mass of the movable portion 7050 in FIG. 7J is 10.2 g, its weight would be approximately 0.1N. If each of the springs 7030 are pre-loaded to a tension of 1N, a maximum variation in a threshold force to move the movable portion 7050 may be approximately 10% of the nominal threshold force ((0.1N+0.1N)/(1N×2)=10%).

Adjustability of a spring rate for example may allow an adjustment of valve behaviour, such as for different users, for a change in prescribed treatment pressure, or for a change in a type of therapy.

4.7.1.2 Damping

One aspect of the present technology relates to damping of a movable portion 7050.

In some forms of the present technology, damping may be added to the movable portion 7050 to improve a stability of the movable portion 7050. For example, the movable portion 7050 may be coupled to, or comprise, a damping material. In another example, a viscous damper may be coupled to the movable portion 7050.

As described above, velocity of the air ($V_{air}$), air pressure in the variable conduit ($P_{conduit}$) and size of the variable conduit ($W_{conduit}$) affect each other in turn if one is changed from equilibrium. Thus, in some forms, addition of damping to the movable portion 7050 may assist to stabilise the movable portion 7050, for example to reduce or prevent oscillation, or 'fluttering' as may occur in a system that may be inadequately damped.

An exemplary schematic of a movable portion 7050 comprising a damper 7040 is shown in FIG. 7I. The movable portion 7050 is shown to comprise two dampers 7040, each located adjacent to a spring 7030. Such a system could be modelled as a mass-spring-damper system for example in order to characterise its behaviour and to determine appropriate spring and/or damper characteristics.

For instance, the movable portion 7050 may be critically damped, underdamped or overdamped in each of a plurality of directions.

4.7.2 Flow Regulating Vent Arrangement

One aspect of the present technology relates to a vent arrangement wherein a flow rate therethough is regulated.

In one form, a vent arrangement may comprise a flow regulating valve. An exemplary flow regulating vent arrangement 7000 is shown in FIG. 7J, comprising a flow regulating valve 7010 located upstream of a set of vent orifices 7100 (one or more vent orifices). A flow of air travelling through the outlet 7014 of the flow regulating valve 7010 may travel downstream and exit through the set of vent orifices 7100 as shown in FIG. 7J.

In another form, a vent arrangement may comprise a flow regulating valve, wherein the movable portion moves to adjust a size of a vent orifice. An exemplary schematic is shown in FIG. 7K and FIG. 7L. It can be seen in FIG. 7K and FIG. 7L that the movable portion 7050 at least partly defines a vent orifice 7110. As the movable portion 7050 deflects according to the air flow through the variable conduit 7016, a size of the vent orifice 7110 is affected.

It is contemplated that other configuration of a vent arrangement may also be suitable to regulate a flow rate therethrough, such as a vent arrangement wherein the movable portion moves to occlude some or a portion of a set of vent orifices, or any number of other configurations.

In a configuration such as those shown in FIG. 7K and FIG. 7L, a vent orifice 7110 and/or a set of vent orifices 7100 may functionally and/or structurally coincide with an outlet of the flow regulating valve 7010.

FIG. 8A shows an exemplary vent arrangement 8000.

The vent arrangement 8000 shown in FIG. 8A comprises a flow regulating valve 8010 and vent orifices 8110. The flow regulating valve 8010 comprises an inlet 8012 configured to receive a flow of air, a variable conduit 8016 defined by a movable portion 8050 and a valve body 8011 and an outlet 8014.

The movable portion 8050 in FIG. 8A may be movable at least in a direction of the double-ended arrows shown in FIG. 8A.

For example, the movable portion 8050 may be movably (e.g. slidably) coupled to the valve body 8011, such as by a slot or a shaft. Alternatively, the movable portion 8050 may be coupled to the valve body 8011 by one or more springs, configured to allow movement in a direction of the double-ended arrows shown in FIG. 8A. Any number of additional or alternative means of course may be also suitable for movably coupling the movable portion 8050 to the valve body 8011.

In some arrangements, the movable portion 8050 may not be coupled to the valve body 8011. For example, as shown in FIG. 8A, the movable portion 8050 may be configured to move freely and independently of the valve body 8011 in all directions within a range of movement. The movable portion 8050 in the example shown in FIG. 8A may be free to move in the lateral direction and downwards direction of the figure until coming into contact with the valve body 8011.

The vent arrangement 8000 may comprise one or more bounding portions to limit a range of travel of the movable portion 8050. For example, the vent arrangement 8000 may comprise means (e.g. flanges, sheaths, covers) to prevent dislodgement of the movable portion 8050 from the vent arrangement 8000 without coupling the movable portion 8050 to the valve body 8011. An exemplary arrangement is shown in FIG. 8I, wherein a retaining flange 8060 is present towards a top of the valve body 8011 to prevent escape or disengagement of the movable portion 8050 from the vent arrangement 8000.

Similarly to the movable portions 7050 in the vent arrangements or flow regulating valves described above, the movable portion 8050 shown in FIG. 8A may move according at least in part to air pressures of the first and the second sides of the movable portion 8050. Thus, the movable portion 8050 shown in FIG. 8A may move in the direction indicated by the double-ended arrows according to the atmospheric pressure $P_{atm}$ and the pressure in the variable conduit $P_{conduit}$.

The movable portion 8050 may at least partly define the variable conduit. For example, the movable portion 8050 may comprise a first surface 8052 that defines a boundary (e.g. top boundary) of the variable conduit 8016. The first surface 8052 may be circular as shown in FIG. 8B and FIG. 8C, although other shapes (e.g. rectangular, square, etc.) may be also suitable. The movable portion 8050 may comprise a plurality of surfaces that define the variable conduit.

Another form of a vent arrangement 8000 is shown in FIG. 8G, wherein the vent arrangement 8000 comprises a spring 8030.

In this form, the spring 8030 may be configured to locate the movable portion 8050 in a radial direction. Additionally, or alternatively, the spring 8030 may provide and/or adjust a threshold load for movement, a spring rate, and/or damping of the movable portion 8050 in one or more directions.

For example, the spring 8030 may be a leaf spring as shown in FIG. 8G. In another example, the spring 8030 may be a plate (e.g. annular plate) as shown in FIG. 8H. The spring 8030 may comprise a resilient, damped material such as silicone. It will be of course understood that other materials or arrangements may be also suitable.

The spring 8030 may be coupled to the movable portion 8050, such as by interference fit. In the arrangement shown in FIG. 8G, the spring 8030 may be inserted into a portion (e.g. a groove) of the movable portion 8050, and may be located via a recess of the spring 8030 that receives a key 8058 from the movable portion 8050. In the arrangement shown in FIG. 8H, the spring 8030 may be adhered to a surface of the movable portion 8050. Any number of other methods of coupling the leaf spring to the movable portion 8050 (e.g. overmoulding, etc.) may be also appropriate.

The spring 8030 may comprise another material, such as a foam material. In the arrangement as shown in FIG. 8H, the spring 8030 may be a foam material configured to provide resilience as well as damping to the movable portion 8050.

The spring 8030 may be coupled to the valve body 8011 as shown in FIG. 8G and FIG. 8H, such as by overmoulding, interference fit, bonding with an adhesive or any other known methods.

Thus the movable portion 8050 may be coupled to the valve body 8011 via the spring 8030, to control a movement of the movable portion 8050. It is noted that the movable portion 8050 may be coupled to another body or structure other than the valve body 8011 via the spring 8030.

FIG. 8J and FIG. 8K show perspective exploded views of a vent arrangement 8000 shown in FIG. 8G.

In some forms, such as where the movable portion 8050 is not constrained in one or more directions, the vent arrangement may comprise a self-centring feature.

For example, the movable portion 8050 may be configured to The first surface 8052 may comprise one or more recesses such as a central recess 8054 as shown in FIG. 8B, FIG. 8C and FIG. 8K. The central recess may be configured to aerodynamically retain the movable portion 8050 in its intended operating position.

For example, the central recess 8054 may be located co-axially with the inlet 8012, and comprise one or more angled surfaces 8056, such as a bevel or a chamfer. The angled surfaces 8056 may be for example at an angle of 45 degrees to an axis of the inlet 8012, however a number of other geometries may also be suitable, according to a design of the inlet 8012 and/or the movable portion 8050.

In some forms, a movement of the movable portion 8050 away from its preferred, central location (e.g. concentric with an axis of the inlet 8012) may increase an amount of air flow acting on an angled surface 8056. Accordingly, due to the orientation of the angled surface 8056, the additional air flow acting on the angled surface 8056 may introduce or increase a restoring force acting on the movable portion 8050.

An exemplary set of illustrations are shown in FIG. 8D, FIG. 8E and FIG. 8F. In each figure, a set of projection lines are drawn projecting the boundaries of the inlet onto the movable portion 8050. The projection lines are drawn as dotted lines, and can be seen to terminate at a first angled surface 8056A or a second angled surface 8056B.

When the movable portion 8050 is centred (e.g. as shown in FIG. 8D), the projection lines meet the angled surfaces 8056A and 8056B substantially symmetrically. Thus, the air travelling through the inlet 8012 is likely to impact the movable portion 8050 substantially symmetrically, imparting a substantially balanced (i.e. zero) overall lateral force onto the movable portion 8050.

FIG. 8E shows a configuration wherein the movable portion 8050 has moved to the right of the figure. As the first angled surface 8056A faces right and down, pressure acting on the surface will result in a force with an upwards component and a leftwards component. Similarly, as the second angled surface 8056B faces left and down, pressure acting on the surface will result in a force with an upwards component and a rightwards component.

It can be seen in FIG. 8E that a greater portion of the first angled surface 8056A is exposed to the air flow from the inlet 8012 in comparison to FIG. 8D. On the other hand, it can be seen in FIG. 8E that a smaller portion of the second angled surface 8056B is exposed to the air flow from the inlet 8012 in comparison to FIG. 8D. Thus, the overall force acting on the movable portion 8050 may comprise an increased leftwards component, tending to restore the movable portion 8050 towards its original, centred position.

FIG. 8F shows a configuration wherein the movable portion 8050 has moved to the left of the figure. It can be seen in FIG. 8F that a smaller portion of the first angled surface 8056A is exposed to the air flow from the inlet 8012 in comparison to FIG. 8D. On the other hand, it can be seen in FIG. 8F that a greater portion of the second angled surface 8056B is exposed to the air flow from the inlet 8012 in comparison to FIG. 8D. Thus, the overall force acting on the movable portion 8050 may comprise an increased rightwards component, tending to restore the movable portion 8050 towards its original, centred position.

FIG. 8L shows another aspect of the technology with a vent arrangement 8000 and housing. The housing includes a base 8150 with one or more posts 8140 (not shown in FIG. 8L) supporting the movable portion 8050. The movable portion 8050 may be in the form of a puck, a vented puck or other shape.

As will be described in further detail elsewhere, a 'vented' puck or movable portion may comprise one or more fixed vents to allow a flow of air therethrough, such as to the atmosphere. Such a movable portion, comprising both fixed vents and variable vents advantageously allows for a combination of aspects of both types of venting in a small, effective package.

The posts 8140 of the base 8150 may include spacers 8130 designed to adjust a starting height of the movable portion 8050. The starting height of the movable portion 8050 is the distance between the movable portion 8050 and the base 8150 when the movable portion 8050 is at a location closest to the base 8150. In other words, the starting height of the movable portion 8050 corresponds to the axial length of the spacers 8130. As can be seen, a minimum size of the vent orifices 8110 is directly related to the starting height set by the spacers 8130.

In addition, a spring 8030 may be positioned on top of the movable portion 8050. A cap 8120 may be secured to the base 8150 to contain the movable portion 8050, the spacers 8130 and the spring 8030. It is contemplated that the vent arrangement 8000 of FIG. 8L may omit the spring 8030 and/or the spacers 8130.

The spring 8030 may comprise one or more active portions configured to deform to move the movable portion 8050. In one form, the spring 8030 may comprise one or more radial channels, such as shown in FIG. 8N and FIG. 8Q, configured to deform to move the deformable portion 8050. A radial channel may comprise a semicircular cross section, such as two as shown in FIG. 8M, facing opposing directions to each other. Thus, the spring 8030 may comprise hemi-toroid shaped active portions. The symmetrical configuration may beneficially allow the movable portion 8050 to traverse vertically in a consistent and predictable manner.

FIG. 8M shows an aspect of the technology with a double vent configuration. The double vent configuration may be similar to the single vent configuration illustrated in FIG. 8L. However, in the double vent configuration, the vent arrangement 8000 may include two movable portions 8050. The movable portions 8050 may be stacked on top of each other to create two levels of vent orifices 8110. It is contemplated that two sets of spacers 8130 may be positioned to set a starting height for both movable portions 8050. In addition, it is contemplated that the spacers 8130 between the movable portions 8050 may be sized differently from the spacers 8130 between the first movable portion 8050 and the base 8150.

It should be understood that although the double vent configuration is illustrated as having two springs 8030, the double vent configuration may include only one spring 8030 positioned between the second spring 8030 and the cap 8120. Alternatively, the single spring 8030 may be positioned between the two movable portions 8050. It is further contemplated that the double vent configuration may have only one set of spacers 8130 or no spacers 8130 at all.

The double vent configuration may have the effect of almost doubling the output of a single vent configuration. For example, for a single vent configuration with all spacers 8130 having axial lengths of 1.25 mm, a 20 mm diameter movable portion 8050 and a 4 mm inlet into the flow regulating valve, the flow of gas vented through the vent arrangement may be 8-9 L/min at 4-20 cmH$_2$O. For the same parameters, a double vent configuration may result in a 15-19 l/min flow rate at 4-20cmH$_2$O.

4.7.3 Flow Characteristics of the Flow Regulating Valve/Vent Arrangement

A flow regulating valve, and/or a flow regulating vent arrangement according to the present technology may be readily designed and tuned such that the flow characteristics therethrough may be optimised.

In an arrangement such as that shown in FIG. 7A, a direction of air flow through the inlet 7012 may be substantially perpendicular to a direction of movement of the movable portion 7050.

As a result, in the variable conduit 7016 shown in FIG. 7A, an increase in velocity may always result in a decrease in air pressure in the variable conduit ($P_{conduit}$). Accordingly, the movable portion 7050 may behave such that an increase in velocity always results in an increase in an impedance of the variable conduit, via a decrease in the width ($W_{conduit}$) of the variable conduit.

In another arrangement such as that shown in FIG. 8A, a direction of air flow through the inlet 8012 may be substantially parallel to a direction of movement of the movable portion 8050. Thus, in the arrangement shown in FIG. 8A, the air flow through the inlet 8012 may act on the movable portion 8050 in an upwards direction to widen the variable conduit 8016. On the other hand, the air flow through the variable conduit 8016 may act to narrow the variable conduit 8016 as a function of an increase in velocity.

Accordingly, in a vent arrangement such as that shown in FIG. 8G, the upwards force due to inlet flow and the downwards force due to conduit flow may be used to provide a vent flow characteristic with rapidly increasing flow rates at low pressures as a function of pressure, and substantially constant flow rates at higher pressures as a function of pressure.

FIG. 9A shows an experimentally derived flow curve for an exemplary vent arrangement, such as one similar to that shown in FIG. 8G. FIG. 9A shows the air flow rate to increase at a steep gradient as a function of pressure to approximately 18.5 L/min, at a pressure of approximately 1.3 cm H$_2$O (see measure 9010). At measure 9020, the flow rate is approximately 20 L/min at an increased pressure of approximately 5 cm H$_2$O. It can also be seen that at 20 cm H$_2$O (see measure 9030), the flow rate has increased to approximately 24 L/min, indicating a decreased rate of increase of flow rate as a function of pressure.

Thus, advantageously, a vent arrangement with a flow characteristic shown in FIG. 9A may reach a minimum flow rate for sufficient washout at a low pressure, while preventing an excessive washout of air through the vent arrangement at a high pressure.

FIG. 9B shows an experimentally derived flow curve for another exemplary vent arrangement, wherein the spring has been modified to allow greater maximum travel in the 'open' direction of the variable conduit. It can be seen here that a low-pressure behaviour (e.g. between 0 and 6 cm H$_2$O) can be varied substantially without greatly modifying the high-pressure behaviour (e.g. between 10 and 20 cm H$_2$O).

For example, at a pressure of approximately 5 cm H$_2$O, it can be seen that the flow rate in the graph shown in FIG. 9B (see measure 9040) is significantly (approximately 50%) higher than that shown in FIG. 9A (see measure 9020), while at a pressure of approximately 20 cm H$_2$O, the flow rate in the graph shown in FIG. 9B (see measure 9040) is slightly lower (approximately 10%) to that shown in FIG. 9A (see measure 9020).

Other parameters of the vent arrangement 8000 may be adjusted to "tune" the characteristics of the vent arrangement 8000. For example, the diameter of the orifice in the base 8150 through which gas enters the flow regulating valve may be adjusted. In addition, the material forming the base 8150 (e.g. polycarbonates, thermoplastic polymers, acrylonitrile butadiene styrene (ABS), thermoplastic resin and silicone) may be adjusted.

In addition, the axial length of the spacers 8130 may be adjusted to "tune" for starting vent flow (L/min) and correct pressure activation. The diameter or largest length of the movable portion 8050 may be adjusted. For example, by reducing the diameter or largest length of the movable portion 8050, the initial low pressure flow rate can be changed to start at a higher flow rate. The material of the movable portion 8050 may also be adjusted to "tune" for noise dampening performance. The movable portion 8050 may be formed of, e.g., polycarbonates, thermoplastic polymers, acrylonitrile butadiene styrene (ABS), thermoplastic resin, thermoplastic elastomers and silicone.

As can be seen in FIG. 10 below, adjusting the parameters of the vent arrangement 8000 so that the diameter of the orifice in the base 8150 through which gas enters the flow regulating valve is 5 mm, the axial height of the spacers 8130 is 1.5 mm and the spring 8030 comprises a 30 Duro material, results in a stable 10 L/min flow.

4.7.3.1 Respiratory Treatment Systems Comprising Flow Regulating Valves/Flow Regulating Vent Arrangements It is contemplated that a respiratory treatment system may comprise a set of flow regulating valves and/or a set of flow regulating vent arrangements.

Thus, one form of a respiratory treatment system may comprise an RPT device, an air circuit, a humidifier, a patient interface and data management wherein the patient interface comprises a flow regulating vent arrangement.

Another form of a respiratory treatment system may comprise an RPT device, a dual-limb air circuit, a humidifier, a patient interface and data management wherein the RPT device comprises a flow regulating vent arrangement. The flow regulating vent arrangement may be configured to exhaust air from an expiratory limb of the dual-limb air circuit.

Another form of a respiratory treatment system may comprise an RPT device, an air circuit, a humidifier, a patient interface and data management, and a flow regulating vent arrangement located between the patient interface and the air circuit.

Some forms of respiratory treatment systems may comprise an RPT device, an air circuit, a humidifier, a patient interface and data management, wherein the patient interface may comprise a vent arrangement, the air circuit may comprise a vent arrangement and a flow regulating valve is located between the patient interface and the air circuit.

It will be thus understood that each of the flow regulating vent arrangements and/or flow regulating valves may be located at one or more locations within the respiratory treatment systems while remaining within the scope of the present technology.

It should also be understood that the components, elements and features of the various flow regulating valves and vent arrangements can be used together in any desired combination or permutation to create new flow regulating valves and vent arrangements. For example, the various movable portions, springs, covers, bases, and spacers are not limited to the configurations in which they are illustrated. The various movable portions, springs, covers, bases, and spacers may be used with any of illustrated flow valves and vent arrangements.

4.8 Glossary

For the purposes of the present technology disclosure, in certain forms of the present technology, one or more of the following definitions may apply. In other forms of the present technology, alternative definitions may apply.

4.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. While flow rate and ventilation have the same dimensions of volume or mass per unit time, flow rate typically refers to an instantaneous quantity unless stated otherwise, and is typically measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. 'Flow rate' is sometimes shortened to simply 'flow'.

Leak: The word leak will be taken to be an unintended flow of air. In one example, leak may occur as the result of an incomplete seal between a mask and a patient's face. In another example leak may occur in a swivel elbow to the ambient.

Noise, vent (acoustic): Vent noise in the present document refers to noise which is generated by the flow of air through any vents such as vent holes in the patient interface.

Patient: A person, whether or not they are suffering from a respiratory disease.

Pressure: Force per unit area. Pressure may be measured in a range of units, including $cmH_2O$, $g\text{-}f/cm^2$, hectopascal. 1 $cmH_2O$ is equal to 1 $g\text{-}f/cm^2$ and is approximately 0.98 hectopascal. In this specification, unless otherwise stated, pressure is given in units of $cmH_2O$, and shall refer to static pressure.

Respiratory Pressure Therapy (RPT): The application of a supply of air to an entrance to the airways at a treatment pressure that is typically positive with respect to atmosphere.

Vent (noun): The structure that allows a flow of air from an interior of the treatment system to ambient air, for example to allow clinically effective washout of exhaled gases.

4.8.2 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

4.8.3 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to separate a body of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

4.8.4 Terms Used in Relation to Mechanical Items

Resilience: Ability of a material to absorb energy when deformed elastically and to release the energy upon unloading.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

4.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 4.10 REFERENCE SIGNS LIST | |
|---|---|
| Item | Reference Numeral |
| patient | 1000 |
| bed partner | 1100 |
| patient interface | 3000 |

4.10 REFERENCE SIGNS LIST

| Item | Reference Numeral |
| --- | --- |
| seal-forming structure | 3100 |
| plenum chamber | 3200 |
| positioning and stabilising structure | 3300 |
| vent | 3400 |
| connection port | 3600 |
| forehead support | 3700 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| pneumatic component | 4100 |
| air filter | 4110 |
| inlet air filter | 4112 |
| outlet air filter | 4114 |
| inlet muffler | 4122 |
| outlet muffler | 4124 |
| pressure generator | 4140 |
| blower | 4142 |
| motor | 4144 |
| air circuit | 4170 |
| supplemental oxygen | 4180 |
| electrical component | 4200 |
| PCBA | 4202 |
| power supply | 4210 |
| input device | 4220 |
| central controller | 4230 |
| therapy device controller | 4240 |
| protection circuit | 4250 |
| memory | 4260 |
| transducer | 4270 |
| pressure sensor | 4272 |
| flow rate sensor | 4274 |
| motor speed transducer | 4276 |
| data communication interface | 4280 |
| output device | 4290 |
| algorithm | 4300 |
| therapy control module | 4330 |
| humidifier | 5000 |
| humidifier inlet | 5002 |
| humidifier outlet | 5004 |
| humidifier base | 5006 |
| humidifier reservoir | 5110 |
| humidifier reservoir dock | 5130 |
| heating element | 5240 |
| flow regulating vent arrangement | 7000 |
| flow regulating valve | 7010 |
| inlet | 7012 |
| outlet | 7014 |
| variable conduit | 7016 |
| entrainment orifice | 7020 |
| spring | 7030 |
| damper | 7040 |
| movable portion | 7050 |
| vent orifice | 7100 |
| vent orifice | 7110 |
| vent arrangement | 8000 |
| flow regulating valve | 8010 |
| valve body | 8011 |
| inlet | 8012 |
| outlet | 8014 |
| variable conduit | 8016 |
| spring | 8030 |
| movable portion | 8050 |
| first surface | 8052 |
| central recess | 8054 |
| angled surface | 8056 |
| key | 8058 |
| flange | 8060 |
| vent orifice | 8110 |
| cap | 8120 |
| spacer | 8130 |
| post | 8140 |
| base | 8150 |
| measure | 9010 |
| measure | 9020 |
| measure | 9030 |
| measure | 9040 |
| measure | 9050 |

The invention claimed is:

1. A valve configured to regulate a flow of gas washout from a patient interface, the valve comprising:
an inlet configured to receive the gas washout from the patient interface;
an outlet configured to expel the gas washout to atmosphere;
a valve body attachable to the patient interface;
a movable portion comprising a first side and a second side; and
a variable conduit configured to convey the gas washout from the inlet to the outlet, the variable conduit being defined at least in part by the valve body and the first side of the movable portion,
wherein the second side of the movable portion is isolated from the flow of gas, and the movable portion is configured so that movement of the movable portion changes an impedance of the variable conduit and is caused by a difference between air pressure on the first side of the movable portion and air pressure on the second side of the movable portion, and
wherein the variable conduit is configured so that a flow rate of the gas washout flowing through the variable conduit increases when a pressure of the gas washout entering through the inlet is relatively low and so that the flow rate of the gas washout is substantially constant when the pressure of the gas washout entering through the inlet is relatively high.

2. The valve as claimed in claim 1, wherein the movable portion is disc-shaped.

3. The valve as claimed in claim 1, wherein the movable portion is biased away from the valve body.

4. The valve as claimed in claim 3, further comprising a spring that biases the movable portion away from the valve body.

5. The valve as claimed in claim 1, wherein the inlet is perpendicular to the variable conduit.

6. The valve as claimed in claim 1, wherein the variable conduit comprises an increasing size from the inlet towards the outlet.

7. The valve as claimed in claim 1, wherein the variable conduit is configured as a cylinder.

8. The valve as claimed in claim 1, further comprising a damper coupled to the movable portion.

9. The valve as claimed in claim 1, wherein the inlet is perpendicular to the first side of the movable portion.

10. The valve as claimed in claim 1, further comprising an entrainment port to entrain atmospheric air using the flow of gas.

11. The valve as claimed in claim 10, wherein the movable portion at least partly comprises the entrainment port.

12. The valve as claimed in claim 1, wherein the valve body and the first side of the movable portion are parallel to each other.

13. The valve as claimed in claim 1, the first side of the movable portion comprising a stabilising recess.

14. The valve as claimed in claim 1, further comprising an additional movable portion positioned adjacent the second side.

15. The valve as claimed in claim 1, wherein the second side of the movable portion is located in ambient air.

16. A patient interface for a respiratory apparatus, the patient interface comprising:
- a seal-forming structure with a seal-forming surface;
- a plenum chamber; and
- the valve as claimed in claim 1, wherein the valve is configured to vent gas from the plenum chamber.

17. The valve as claimed in claim 1, wherein the movable portion is configured to move upon the difference between the air pressure on the first side of the movable portion and the air pressure on the second side of the movable portion being greater than a predetermined minimum threshold.

18. The valve as claimed in claim 1, wherein the variable conduit is configured so that the flow rate of the gas washout flowing through the variable conduit increases when the pressure of the gas washout entering through the inlet is less than a threshold pressure range and the flow rate of the gas washout flowing through the variable conduit is substantially constant when the pressure of the gas washout entering the inlet is above the threshold pressure range.

19. A vent arrangement for washout of gases from a patient interface, the vent arrangement comprising:
- a gas inlet configured to receive gas washout from the patient interface;
- a gas outlet configured to expel the gas washout to atmosphere;
- a valve comprising a flow surface and a reference surface;
- a valve housing; and
- a conduit configured to deliver the flow of gas from the gas inlet to the gas outlet, the conduit being defined at least partly by the flow surface and the valve housing, wherein the reference surface is separated from the flow of gas and the valve is movable to vary a size of the conduit, the valve being configured so that the movement of the valve is caused by a pressure differential between a pressure acting on the flow surface and a pressure acting on the reference surface, and
wherein the conduit is configured so that a flow rate of the gas washout flowing through the conduit increases when a pressure of the gas washout entering through the gas inlet is relatively low and so that the flow rate of the gas washout flowing through the conduit is substantially constant when the pressure of the gas washout entering through the gas inlet is relatively high.

20. The vent arrangement as claimed in claim 19, wherein the flow surface is disc-shaped.

21. The vent arrangement as claimed in claim 19, wherein the conduit is cylindrically shaped.

22. The vent arrangement as claimed in claim 21, wherein the gas outlet is disposed on a circumference of the cylindrically shaped conduit.

23. The vent arrangement as claimed in claim 19, wherein the valve is configured to move upon the difference between the pressure acting on the reference surface and the pressure acting on the flow surface being greater than a predetermined minimum threshold.

24. The vent arrangement as claimed in claim 19, wherein the conduit is configured so that the flow rate of the gas washout flowing through the conduit increases when the pressure of the gas washout entering through the gas inlet is less than a threshold pressure range and the flow rate of the gas washout flowing through the conduit is substantially constant when the pressure of the gas washout entering the gas inlet is above the threshold pressure range.

* * * * *